(12) United States Patent
Li

(10) Patent No.: US 11,517,274 B2
(45) Date of Patent: Dec. 6, 2022

(54) HYBRID DETECTION SYSTEMS AND METHODS FOR C-ARM INTERVENTIONAL X-RAY SYSTEMS

(71) Applicant: Wisconsin Alumni Research Foundation, Madison, WI (US)

(72) Inventor: Ke Li, Middleton, WI (US)

(73) Assignee: Wisconsin Alumni Research Foundation, Madison ( * ) Notice: Subject to any disclaimer, the term of this patent is extended or adjusted under 35 U.S.C. 154(b) by 252 days.

(21) Appl. No.: 16/890,960

(22) Filed: Jun. 2, 2020

(65) Prior Publication Data

US 2021/0369219 A1 Dec. 2, 2021

(51) Int. Cl.
*A61B 6/00* (2006.01)
*A61B 6/03* (2006.01)

(52) U.S. Cl.
CPC .......... *A61B 6/4241* (2013.01); *A61B 6/032* (2013.01); *A61B 6/4405* (2013.01); *A61B 6/4441* (2013.01); *A61B 6/461* (2013.01); *A61B 6/487* (2013.01); *A61B 6/5205* (2013.01)

(58) Field of Classification Search
CPC ....... A61B 6/461; A61B 6/4441; A61B 6/487; A61B 6/032; A61B 6/4405; A61B 6/4411; A61B 6/5205; A61B 6/4241; A61B 6/035; A61B 6/4085; A61B 6/4266; A61B 6/4233; A61B 6/4283; A61B 6/4417; A61B 6/40; A61B 6/42; A61B 6/583; A61B 6/4429; A61B 6/037; A61B 6/52; A61B 6/547; A61B 6/545; A61B 6/4208; A61B 6/482; A61B 6/4035; A61B 6/585; A61B 6/06; A61B 6/486; A61B 6/5235; A61B 6/025; A61B 6/504; A61B 6/5223; A61B 6/5258; G01N 23/046; G01N 2223/401; G01N 23/044; G06T 11/005; G06T 11/006; G06T 2211/424; G06T 2211/408; G06T 2211/421; G06T 11/008; G06T 7/11; G06T 7/187; G06T 7/337; G06T 7/38; G06T 2207/10081; G06T 2207/20221; G06T 2207/20224; G06T 2210/41; G06T 2211/404; A61N 5/1077; A61N 2005/1061; A61N 5/1049; G01T 1/36
USPC ....................................... 378/4, 19, 98.9, 62
See application file for complete search history.

(56) References Cited

U.S. PATENT DOCUMENTS

| | | | |
|---|---|---|---|
| 7,372,934 B2 | 5/2008 | De Man et al. | |
| 9,861,324 B2 | 1/2018 | Wang et al. | |
| 2010/0310044 A1* | 12/2010 | Manak | A61B 6/032 378/198 |

(Continued)

OTHER PUBLICATIONS

Ren, L. et al. "Tutorial on X-ray photon counting detector characterization." Journal of X-ray science and technology 26.1 (2018): 1-28.

*Primary Examiner* — Irakli Kiknadze
(74) *Attorney, Agent, or Firm* — Quarles & Brady LLP

(57) ABSTRACT

Hybrid detection systems and methods for C-arm interventional x-ray systems are provided. The hybrid detection system can have a changeable x-ray detection system that is coupled to an integrated within a C-arm x-ray imaging system. The changeable x-ray detector system can include an energy-integrating x-ray detector, and a photon-counting x-ray detector. The C-arm x-ray imaging system using only one detector at a time to acquire x-ray imaging data.

26 Claims, 15 Drawing Sheets

(56) References Cited

U.S. PATENT DOCUMENTS

| | | | |
|---|---|---|---|
| 2014/0105370 A1* | 4/2014 | Yamakawa | G01T 1/171 378/207 |
| 2015/0103970 A1* | 4/2015 | Chen | G01N 23/046 378/62 |
| 2015/0348258 A1* | 12/2015 | Petschke | A61B 6/5258 378/19 |
| 2015/0363947 A1* | 12/2015 | Rigie | G06T 11/005 382/131 |
| 2016/0371862 A1* | 12/2016 | Silver | G06T 7/11 |
| 2017/0212250 A1* | 7/2017 | Jin | G01T 1/247 |
| 2017/0249758 A1* | 8/2017 | Mistretta | A61B 6/487 |

* cited by examiner

HYBRID DETECTION SYSTEMS AND METHODS FOR C-ARM INTERVENTIONAL X-RAY SYSTEMS

CROSS-REFERENCE TO RELATED APPLICATIONS

Not applicable.

STATEMENT REGARDING FEDERALLY SPONSORED RESEARCH

Not applicable.

BACKGROUND

Interventional radiology procedures are minimally invasive procedures conducted in an interventional radiology suite. Typical interventional radiology suites are equipped with C-arm x-ray systems that allow the interventional radiologist (or other practitioner) to acquire images during the interventional procedure by rotating the source and detector about the patient using the C-arm. Examiners of interventional radiology procedures include routine procedures such as angioplasties, stent placements, coil embolization, mechanical thrombectomy, liver tumor ablations, rental artery angioplasties, etc., and potentially lifesaving procedures that can include the treatment of intracranial hemorrhages, ischemic strokes, aneurysms, arteriovenous malformations, and so on.

Typical C-arm x-ray systems utilize energy-integrating detectors (EIDs), which generate a signal proportional to the total energy deposited by all photons without specific information about an individual photon or its energy. While these C-arm x-ray systems are the typical choice for conducting interventional radiology procedures, they have limited capabilities compared to, for example, diagnostic, fixed-gantry computed tomography (CT) systems. This is generally because the C-arm systems compromise speed and sophistication available in fixed-gantry CT systems in favor of the openness/accessibility and flexibility provided by the C-arm architecture. That is, in an interventional suite, access to the patient is a necessity and the C-arm architecture and systems provide that access, despite requiring compromises relative to the capabilities of fixed-gantry CT systems.

Thus, it would be desirable to provide interventional x-ray systems that are able to provide greater features and sophistication of imaging capabilities, but without sacrificing the patient access that is a necessity in the interventional radiology suite.

SUMMARY OF THE DISCLOSURE

The present disclosure provides systems and methods that overcome the aforementioned drawbacks by providing hybrid detection systems and methods for C-arm interventional x-ray systems. As will be described, systems and methods are provided that allow a C-arm x-ray imaging system to utilize both an energy-integrated detector, and a photon-counting detector. Enabling the usage of both imaging detectors can allow for better interventional radiology results, as the practitioner can selectively choose which detector to utilize, thereby leveraging the advantages that some types of detectors have with particular imaging tasks, as will be described below.

In some aspects of the disclosure, a C-arm x-ray imaging system is provided that includes a gantry formed as a C-arm configured to pivot about a pivot axis, an x-ray source coupled to a first end of the C-arm, the x-ray source configured to emit x-rays along a path extending to define an axial axis, and a changeable x-ray detector system coupled to a second end of the C-arm arranged in the axial axis, the changeable x-ray detector system configured to receive x-rays emitted from the x-ray source along the path. The changeable x-ray detector system includes an energy-integrating x-ray detector having an array of x-ray sensing elements that are configured to sense x-rays emitted from the x-ray source, a photon-counting detector having another array of x-ray sensing elements configured to determine an interaction between individual x-ray photons from the x-ray source and individual sensing elements of the another array of x-ray sensing elements, and a mounting system configured to move at least one of the energy-integrating detector or the photon-counting detector between a first position in the path to receive the x-rays emitted from the x-ray source and a second position removed from the path to not receive the x-rays emitted from the x-ray source. Only one of the energy-integrating detector and the photon-counting detector is configured to receive the x-rays emitted from the x-ray source at a time.

In another aspect of the disclosure, a method is provided for controlling a C-arm x-ray imaging system that includes a gantry formed as a C-arm, an x-ray source, and a changeable x-ray detector assembly having an energy-integrating detector, and a photon-counting detector. The method includes acquiring first x-ray imaging data, using a processor in communication with the C-arm x-ray imaging system, and only the energy-integrating x-ray detector and acquiring second x-ray imaging data, using the processor, and only the photon-counting detector.

In still another aspect of the disclosure, a method of retrofitting a C-arm x-ray imaging system is provided. The method includes providing the C-arm x-ray imaging system having a gantry formed as a C-arm, an x-ray source assembly coupled to one end of the C-arm, the x-ray source assembly defining an axial axis that intersects the x-ray source assembly, and an x-ray detector assembly coupled to a second end of the C-arm, the x-ray detector having an energy-integrating detector configured to sense x-rays by energy integration over time. The method further includes installing a photon-counting detector to the second end of the C-arm.

In yet another aspect of the disclosure, a C-arm x-ray imaging system is provided that includes a gantry formed as a C-arm configured to pivot about a pivot axis, an x-ray source coupled to a first end of the C-arm to emit x-rays along a path extending to define an axial axis, and both a photon-counting detector and an energy-integrating detector coupled to the second end of the C-arm. The photon-counting detector has a photon-counting sensing surface defined by an array of sensing elements that is smaller than an energy-integrating sensing surface defined by an array of energy-integrating sensing elements of the energy-integrating detector.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTIONS OF THE DRAWINGS

DETAILED DESCRIPTION

Figure 1:
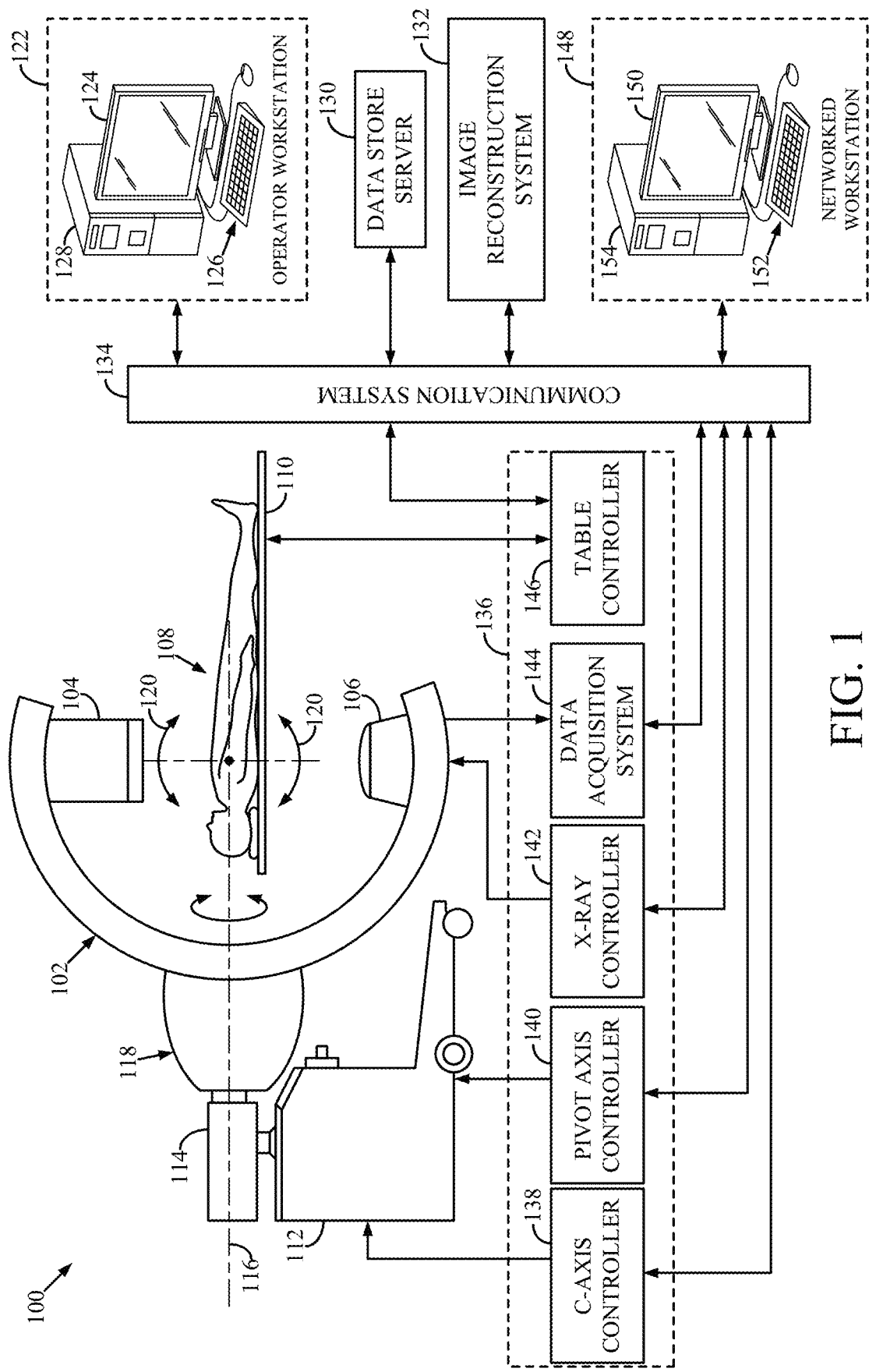
FIG. 1 is a block diagram of an exemplary "C-arm" x-ray imaging system in accordance with the present disclosure.

As detailed above, typical C-arm x-ray systems have an energy-integrating x-ray detector that senses emitted x-rays by integrating the (sensed) x-ray energy over a period of time. While these energy-integrating x-ray detectors can be particularly well-suited for some imaging tasks, such as, during fluoroscopy, for digital subtraction angiography ("DSA") sequences, and for three-dimensional ("3D") cone beam computed tomography ("CBCT") acquisitions, these energy-integrating x-ray detectors can be ill-suited for other imaging tasks. For example, energy-integrating x-ray detectors are particularly insufficient for procedures that require high spatial resolution (e.g., at least due to the relatively bigger pixel element sizes) or quantitative material (e.g. iodine) information.

Another type of x-ray detector is a photon-counting detector, which is typically implemented with a conventional CT scanner having a bore that houses an x-ray source and detector assembly (e.g., that both rotate around a single axis of rotation). Photon-counting detectors are different than energy-integrating x-ray detectors in that they can spatially discriminate individual x-ray photons (emitted from the x-ray source) generating signals that are proportional to the energy of the x-ray photon. In other words, individual sensors (e.g., pixel elements) of the photon-counting detector can determine individual x-ray photons and their corresponding energies. Conversely, for energy-integrating x-ray detectors, a given x-ray photon that is directed at a given individual sensor (e.g., a pixel element) of the energy-integrating x-ray detector is sensed as a peak in time, with the given x-ray photon possibly also being sensed (partially) by adjacent sensors (e.g., from the given x-ray photon being absorbed by the scintillator and remitted in all directions as light sensed by the sensors). Thus, due to the ability of individual x-ray photon discrimination for the photon-counting detectors, the size of individual sensors can be reduced, which can greatly improve image resolution to effectively discern small structures of a subject when utilizing x-ray photon-counting detectors.

Although some conventional CT scanners have adopted photon-counting detectors, photon-counting detectors have not been widely adopted in interventional radiology suites. For example, while photon-counting detectors have better spatial resolution than energy-integrating x-ray detectors, the energy-integrating x-ray detectors are generally better for a greater number of different imaging tasks than the photon-counting detectors (e.g., at least due to the greater sensitivity of the energy-integrating x-ray detectors). So, many interventional radiology suites being able to only have a single x-ray system (e.g., due to cost constraints) prefer to have the energy-integrating x-ray detector system. As another example, some imaging tasks require a CT cone beam (e.g., for a 3D image acquisition). This would then require replacing the energy-integrating x-ray detector with a photon-counting detector of a similar spatial footprint, which would be far more costly. Thus, at least due to costs, and the decrease in quality (or inability) to complete particular imaging tasks, interventional x-ray systems have not adopted the photon-counting x-ray detectors.

Some non-limiting examples of the disclosure provide improved x-ray detection systems for use in an interventional radiology suite. For example, some non-limiting examples of the disclosure provide a C-arm x-ray imaging system having a gantry formed as a C-arm, an x-ray source assembly coupled to one end of the C-arm, and an x-ray detector assembly coupled to an opposing end of the C-arm. The x-ray detector assembly includes both an energy-integrating x-ray detector (e.g., having a scintillator), and a photon-counting detector. By having both detectors, the interventional radiologist (or other practitioner) can select between particular x-ray imaging acquisition modes either using the energy-integrating x-ray detector, or the photon-counting detector, which prevents the undesirable trade-offs of having one x-ray system having one type of the detector over the other. This can be particularly advantageous in that the interventional radiologist can leverage the particular advantages of one detector over the other for specific imaging tasks. For example, the photon-counting detector can be used for discriminating iodine staining in the brain from intracranial hemorrhage, and the energy-integrating x-ray detector can be used for fluoroscopy. These selective imaging modes using the different detectors can free up hospital resources generally, and can importantly prevent undesirable movement of the patient (e.g., the patient does not have to be moved to a different scanner, or room).

In the non-limiting example of FIG. 1, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination that is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors, in which the detector array panel may be around centimeters in size. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124, one or more input devices 126, such as a keyboard and mouse, and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 132 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150, one or more input devices 152, such as a keyboard and mouse, and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Figure 2:
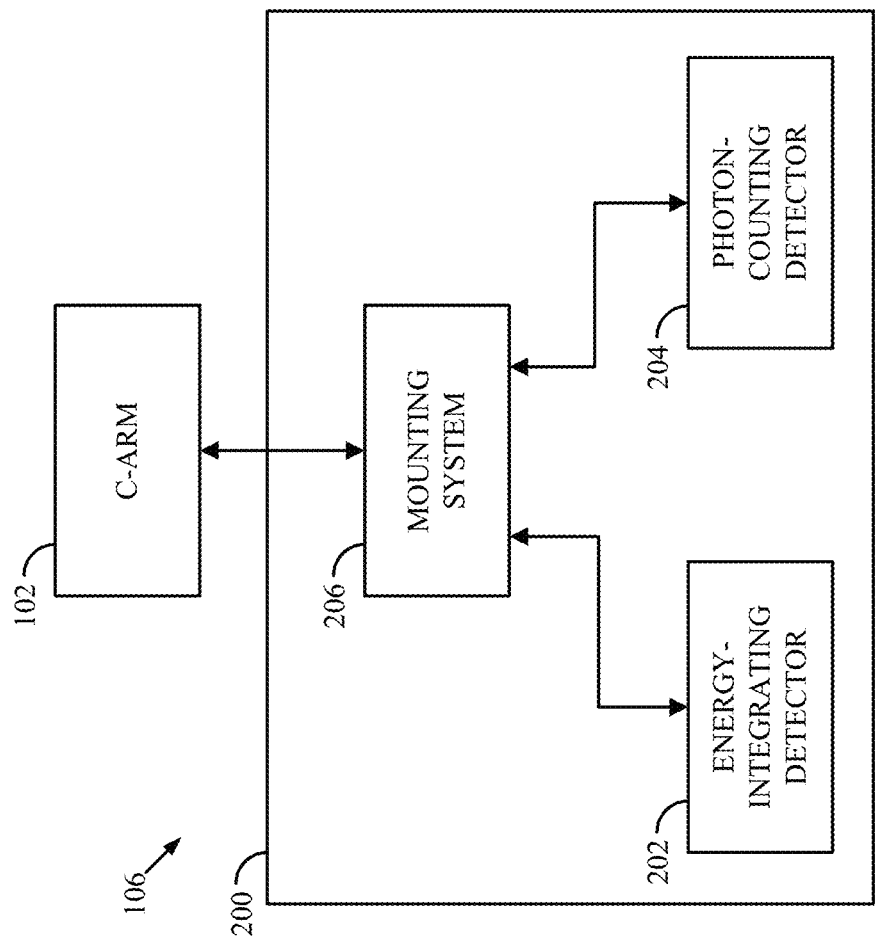
FIG. 2 is a schematic illustration of an example of a changeable x-ray detector system integrated with the C-arm of the C-arm x-ray imaging system of FIG. 1.

FIG. 2 shows a schematic illustration of an example of a changeable x-ray detector system 200 of the detector assembly 106. The changeable x-ray detector system 200 can be similar to the x-ray detection system 106 in that changeable x-ray detector system 200 can also be in communication with the data-acquisition system 144, and can replace the detection system 106 of the C-arm x-ray imaging system 100, generally. The changeable x-ray detection system 200 includes an energy-integrating x-ray detector 202 that can sense x-rays emitted from the x-ray source assembly 104 in the energy integrated manner (as previously described), and a photon-counting detector 204 configured to sense x-rays emitted from the x-source assembly 104 and determine individual x-ray photons and their corresponding energies (as previously described).

The changeable x-ray detection system 200 also includes a mounting system 206. The mounting system 206 can be implemented in different ways. For example, the mounting system 206 can be configured to couple the energy-integrating x-ray detector 202, the photon-counting detector 204, or both to the end of the C-arm 102. In this configuration, either of the detectors 202, 204 can be moved (e.g., translated), so that one of the detectors 202, 204 receives x-rays from the x-ray source assembly 104 while the other detector 202, 204 does not receive the x-rays from the x-ray source assembly 104. Similarly, as desired, the detector 202, 204 that did not receive x-rays previously can be moved again to receive x-rays, effectively blocking the other detector 202, 204 from receiving x-rays (e.g., the other detector 202, 204 does not receive x-rays). In more specific implementations, one of the detectors 202, 204 can be fixed to the end of the C-arm 102 (e.g., by using fastening assemblies, such as fasteners and threaded holes), and the other detector 202, 204 can be supported and suspended by the mounting system 206, where the mounting system 206 can allow translation of the other detector 202, 204 (e.g., the moveable detector 202, 204). In particular, the fixed detector 202, 204 can have a peripheral edge, and the mourning system 206 can allow (or drive) translation of the movable detector 202, 204 such that when the movable detector 202, 204 is not in use the entire moveable detector 202, 204 can be moved past the peripheral edge of the fixed detector 202, 204. This can desirably prevent any blocking of the movable detector 202, 204 from x-rays being received by the fixed detector 202, 204 when the fixed detector 202, 204 is desired to be used. Then, as desired (e.g., for a different imaging procedure), the movable detector 202, 204 can be moved in front of the fixed detector 202, 204, when the practitioner desires to use the movable detector 202, 204.

In some non-limiting examples, in this configuration with both detectors 202, 204 being coupled to the end of the C-arm 102, the moveable detector 202, 204 can be quickly and easily moved to quickly change the different imaging modes, to accommodate quickly changing patient conditions, which can be seen in the interventional radiology suite. As described below, a practitioner can physically move (or translate) one of the detectors 202, 204 into, or out of position, and when in the desired position the practitioner can mechanical lock the position of the moved detector 202, 204 (e.g., with screws, bolts, locks generally, etc.). In other cases, the practitioner can simply instruct (e.g., with a suitable computing device) the detector 202, 204 to move relative to the other detector 202, 204, which can rely on electrical motors, or other electrically actuatable devices.

The mounting system 206 that allows for movement of the moveable detector 202, 204 can be implemented in a variety of different ways. For example, the mounting system 206 can include a rail system, hinges, a bracket system, a socket, a telescoping system, an actuator, a pulley system, a belt system, and the like, to guide or forcibly (such as actively) retract or extend the moveable detector 202, 204 relative to the fixed detector 202, 204. In some non-limiting examples, the mounting system 206 that actively retracts or extends the moveable detector 202, 204 relative to the fixed detector 202, 204 can include motorized and electrically controllable components, such as electric motors, electric actuators, and the like, that can be activated (or locked) by a suitable computing device such as the operator workstation 122. In some configurations, the mounting system 206 can include hard mechanical and/or optoelectronic stops, to prevent movement of the moveable detector 202, 204 once reaching the desired position. These mechanical stops can also be particularly desirable to prevent a need for advanced calibration of the moveable detector 202, 204 when the moveable detector 202, 204 is desired to be imaged with.

As another example, the mounting system 206 can allow each of the detectors 202, 204 to be removably coupled to the end of the C-arm 102. In particular, one detector 202, 204 can be coupled to the end of the C-arm 102 when desired to image using the one detector 202, 204, where the other detector 202, 204 is moved away (e.g., placed away, secured elsewhere to the C-arm 102, stored in a secure location, etc.). Then, when desired to image with the other detector 202, 204, the one detector 202, 204 is removed from the end of the C-arm 102, and the other detector 202, 204 is coupled to the end of the C-arm 102. This configuration can include fasteners generally (e.g., threaded holes and bolts), brackets, sockets and corresponding protrusions (and in some cases, clips on the protrusions), recesses and protrusions and springs, etc.

In some specific implementations, the energy-integrating detector 202 can have a surface (e.g., a detection surface such as the detector array surface) that is larger than a surface (e.g., a detection surface such as the detector array surface) of the photon-counting detector 204. This can be particularly advantageous in that substantially larger imaging surfaces (e.g., sizes of detector arrays) are required for imaging tasks typically conducted by the energy-integrating detector 202 (e.g., 2D radiographic or fluoroscopic acquisitions, cone beam CT or other 3D acquisitions), while imaging tasks conducted by the photon-counting detector 204, for example, reducing metal artifacts in the close proximity of metallic implants or assessing intracranial hemorrhage only requires a relatively small spatial footprint of the detector. The significant decrease in size of the photon-counting detector panels saves a considerable amount of cost for the entire system, as typically the larger the photon-counting detector, the higher the cost. Additionally, the photon-counting detectors generally require large amounts of computing power, which can strain computational recourses of the C-arm x-ray imaging system (e.g., because each photon event and its corresponding energy ideally have to be registered, and there are many photon events that happen within a second for each sensing element). So, having a photon-counting detector that replaces the currently sized energy-integrating x-ray detectors can prevent the ability of real-time usage of the C-arm x-ray system, which is undesirable for an interventional radiology suite that requires real-time implementation, or relatively short periods of delay. Thus, by decreasing the size of the photon counting detectors to be smaller than the conventionally sized energy-integrating detectors, real-time usage of this photon-counting detector can be facilitated.

As shown in FIG. 2, the energy-integrating detector 202 and the photon-counting detector 204 are discrete detectors that can be selectively utilized as desired. The discrete nature of these detectors offer a few significant advantages. First, since these detectors have been around for a number of years, the scientific and other engineering difficulties related to these detectors have been solved to the point of being integrated and accepted within the medical field. For example, each of these detectors have the confidence of medical professionals. Thus, this type of system can be rapidly integrated within imaging suites, and the practitioners using these machines can have the confidence they need to effectively perform a specific procedure using this imaging equipment. Conversely, other integrated types of detectors, such as a single detector having both energy integration-detector sensing elements, and photon-counting detector sensing elements can require extensive mathematical manipulations, overly simplified engineering assumptions, imaging inaccuracies (e.g., when a photon contacts the interface between two types of components), attenuation issues (e.g., when detector arrays are stacked on top of one another), among other issues. Thus, the changeable x-ray detection system 200 offers significant advantages with relatively small obstacles to being readily implemented and accepted by practitioners.

Figure 3:
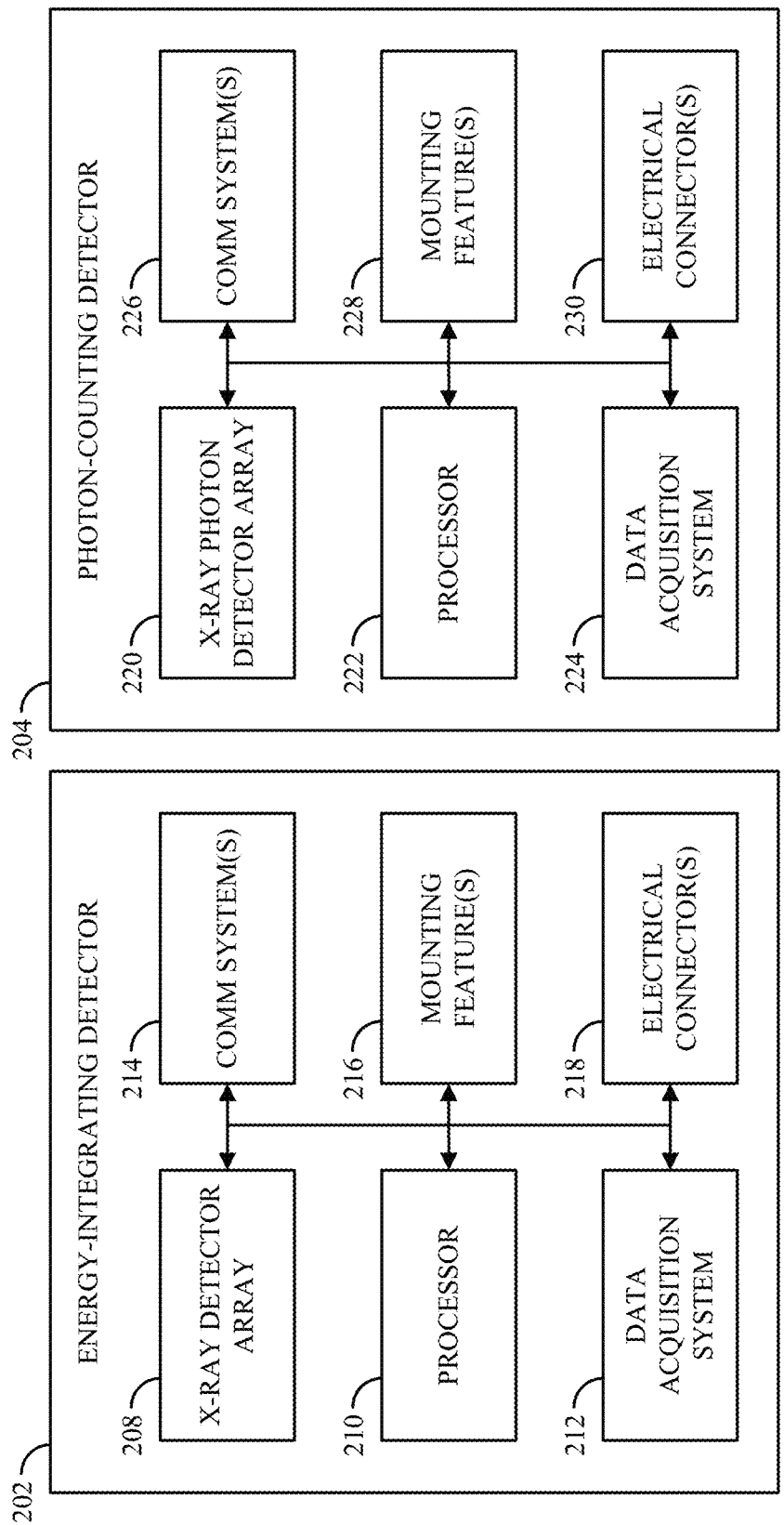
FIG. 3 is a schematic illustration of an energy-integrating detector, and a photon-counting detector of the changeable x-ray detector system of FIG. 2.

FIG. 3 shows schematic illustrations of one, non-limiting example of the energy-integrating detector 202, and the photon-counting detector 204. The energy-integrating detector 202 can include an x-ray detector array 208, a processor device 210, a data acquisition system 212, a communication system 214, mounting feature(s) 216, and electrical connector(s) 218. The x-ray detector array 208 can include an array of sensing elements, and a layer of a scintillator disposed on the array of sensing elements. The processor device 210 can control specific features of the energy-integrating detector 202. For example, the processor device 210 can cause the data acquisition system 212 to acquire x-ray imaging data. As another example, the processor device 210 can implement some or all of the processes (or methods) described in the present disclosure. The processor device 210 can be any suitable hardware processor or combination of processors, such as a central processing unit ("CPU"), a graphics processing unit ("GPU"), etc., which can execute a program (e.g., retrieved from memory, not shown), including for one or more of the processes described below.

In some non-limiting examples, the energy-integrating detector 202 can include a data acquisition system 212, which is separate to the data acquisition system 144. The data acquisition system 212 can sample data from x-ray detector array 208 and can convert the data to digital signals for subsequent processing. For instance, digitized x-ray data is communicated from the data acquisition system 212 to the data storage server 130 or other suitable computing device such as the operator workstation 122 (e.g., via the communication system 214).

In some non-limiting examples, the energy-integrating detector 202 can include one or more communication systems 214. The one or more communication system(s) 214 can include any suitable hardware, firmware, or software for communicating with components external to the energy-integrating detector 202. For example, the communications system(s) 214 can include one or more transceivers, one or more communication chips or chip sets, etc. In a more particular example, communications system(s) 214 can include hardware, firmware or software that can be used to establish a coaxial connection, a fiber optic connection, an Ethernet connection, a universal serial bus ("USB") connection, a Wi-Fi connection, a Bluetooth connection, a cellular connection, a serial interface connection (e.g., Serial Peripheral Interface ("SPI"), or Inter-Integrated Circuit ("I$^2$C")), etc.

In some non-limiting examples, the energy-integrating detector 202 can include mounting feature(s) 216, which can be implemented in various ways that depend on the implementation of the mounting system 206. For example, the mounting features 216 can include a support beam coupled to the energy-integrating detector 202 having a wheel (or bearing) coupled thereto. The wheel can be received within a track of the mounting system 206 to guide translation of the energy-integrating detector 202. As another example, the mounting features 216 can include threaded bores and corresponding fasteners (e.g., bolts) that threadingly engage the energy-integrating detector 202 and are received within threaded bores of the end of the C-arm 102 to securely fasten the energy-integrating detector 202 to the C-arm 102. As yet another example, the mounting features 216 can simply be a (or more) threaded bores that threadingly receive a screw of a linear actuator. This way, the energy-integrating detector 202 can be extended and retreated as desired (e.g., by commands from a suitable computing device).

In some non-limiting examples, the energy-integrating detector 202 can include electrical connector(s) 218. The electrical connectors 218 can generally allow electrical communication between the C-arm imaging system 100 and the components of the energy-integrating detector 202. For example, in some configurations of the energy-integrating detector 202, the energy-integrating detector does not include the processor 210, the data acquisition system 212, or the communication systems 214. So, in this configuration, the electrical connectors 218 allow the energy-integration detector 202 to leverage electrical components already present in the C-arm imaging system 100, such as, for example, power sources to provide power (if needed) to the x-ray detector array 208, the DAS 144, the communication system 134, etc.

Although not shown, the energy-integrating detector 202 can include other typically used computing and electrical components, such as, power sources, memory (e.g., that can include any suitable volatile memory, non-volatile memory, storage, or any suitable combination thereof), etc.

As shown, the photon counting detector 204 can include many of the previously described components, particularly with regard to the energy-integrating detector 202. For example, aside from the x-ray photon detector array 220, the photon-counting detector 204 can also include a processor device 222, a data acquisition system 224, a communication system 226, mounting feature(s) 228, and electrical connector(s) 230. These components are similar to the components of the energy-integrating detector 202, and thus the previous descriptions of these components are also applicable to the photon-counting detector 204. The x-ray photon detector array 220 includes an array of sensing elements and a semiconductor (doped) layer coupled to the array of sensing elements, which is able to discriminate individual x-ray photons (emitted from the x-ray source) generating signals that are proportional to the energy of the x-ray photon that interacts with the semiconductor layer. Thus, the x-ray photon detector array 220 can determine (or otherwise) generate a spatial energy spectrum by keeping track of the number and energies of each x-ray photon event location. Thus, the photon-counting detector 204 can implement spectral CT.

Figure 4:
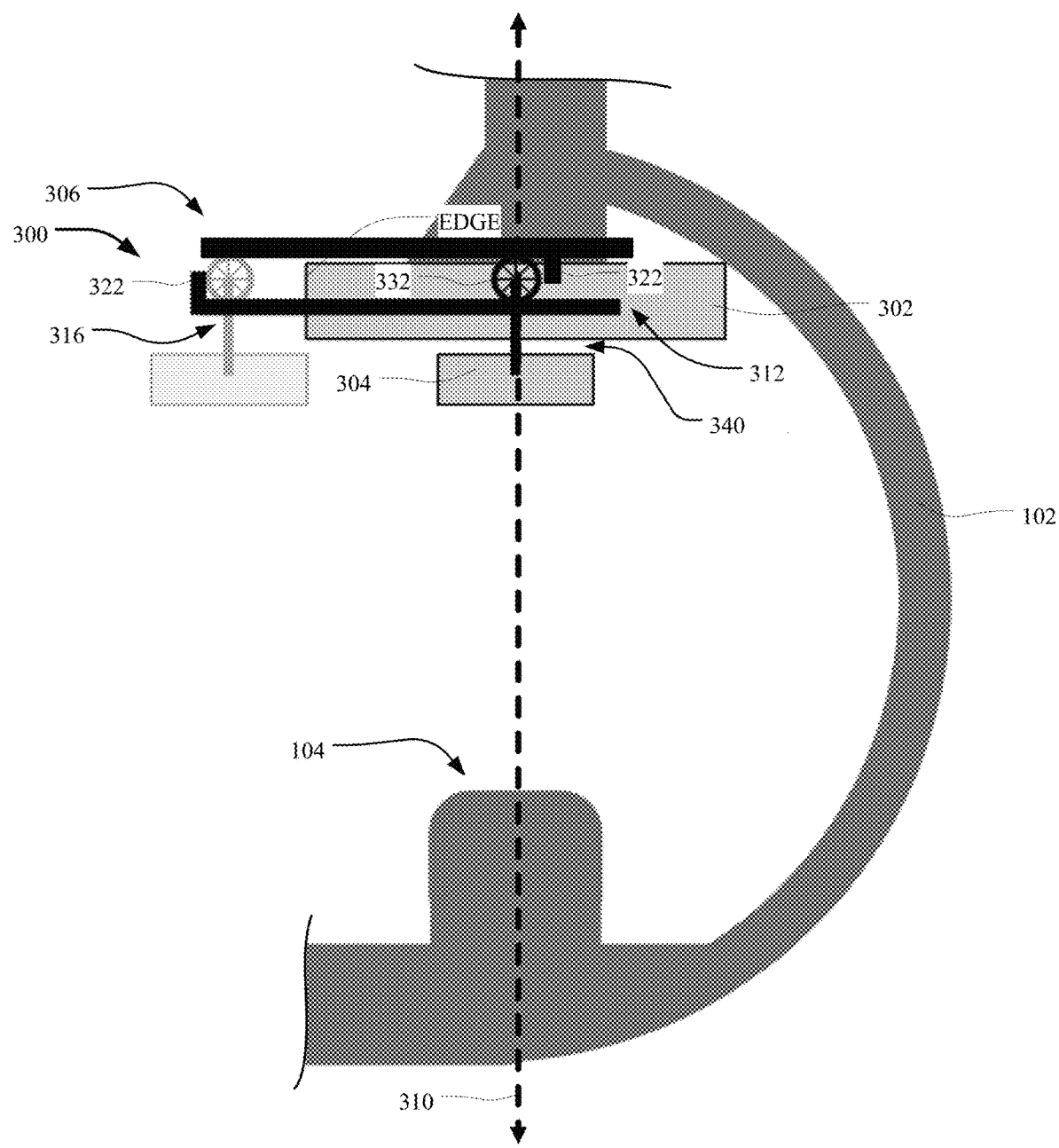
FIG. 4 is an illustration of another example of a changeable x-ray detector system integrated with and coupled to the C-arm of the C-arm x-ray imaging system of FIG. 1.
Figure 5:
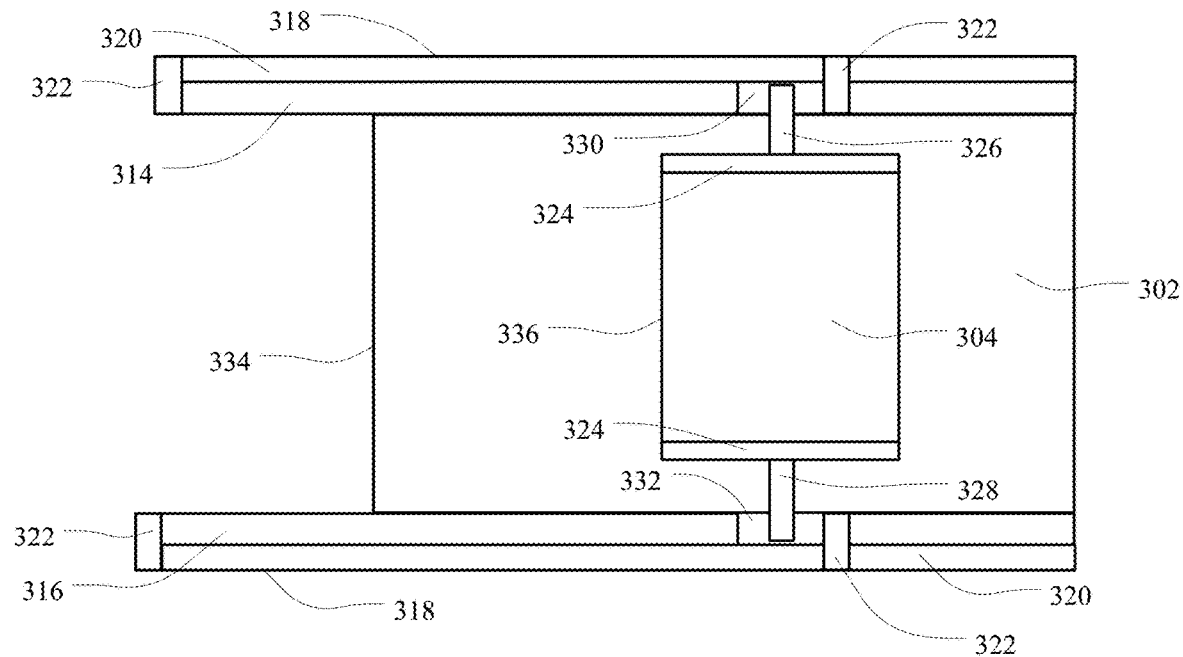
FIG. 5 is a bottom view of the photon-counting detector of the changeable x-ray detector system of FIG. 4 in a first configuration.

FIGS. 4 and 5 show another example of a changeable x-ray detector system 300 coupled to and integrated with the C-arm x-ray imaging system 100. The changeable x-ray detector system 300 includes an energy-integrating detector 302 that is fixed to an end of the C-arm 102, a photon-counting detector 304, and a mounting system 306. As shown, the changeable x-ray detector system 300 is coupled to an end of the C-arm 102 opposite the x-ray source assembly 104. The x-ray source assembly 104 is configured to emit x-rays towards the changeable x-ray detector system 300 along a path that extends to define an axial axis 310. The mounting system 306 includes a rail system 312 that has a first track 314, and a second track 316 opposite the first track 314. Both tracks 314, 316 are coupled to the end of the C-arm 102, and each track 314, 316 has a wall 318 (not shown in FIG. 4), and a flange 320 that both define a corresponding channel of each respective track. Mechanical and/or optoelectronic stops 322 are located at two locations on each track 314, 316 and are implemented as extensions (or protrusions) of the respective track that limit the translation of the photon-counting detector 304 as described in more detail below.

As shown, the photon-counting detector 302 has a housing 324, axles 326, 328, and motorized wheels 330, 332. One end of the axle 326 is coupled to one end of the housing 324 via a u-shaped (or L-shaped, or curved) member and the opposing end is interfaced with the motorized wheel 330. Similarly, one end of the axle 328 is coupled to an opposing end of the housing 324 via a u-shaped member (or L-shaped, or curved) and the other end of the axle 328 is interfaced with the motorized wheel 332. The motorized wheels 330, 332 are situated on their respective tracks 314, 316 and when activated allow the photon-counting detector 304 to translate along the tracks 314, 316. The motorized wheel 330 is situated within the track 314 such that one end of the motorized wheel 330 contacts the lower surface of the track 314, and the opposing end of the motorized wheel 330 contacts a surface of the respective flange 320. Similarly, the motorized wheel 332 is situated within the track 316 such that one end of the motorized wheel 332 contacts a lower surface of the track 314 and the opposing end of the motorized wheel 332 contacts a surface of the respective flange 320. As shown, both flanges 320 extend towards the photon-counting detector 304 such that a portion (or all) of the respective motorized wheels 330, 332 are retained between the respective flange 320 and the lower surface of the respective track 314, 316. This way, as the C-arm 102 rotates, the photon-counting detector 304 is constrained from moving towards or away from the x-ray source detector 104 along the axial axis 310.

In some non-limiting examples, each of the motorized wheels 330, 332 include an electric motor that can be instructed by the processor of the photon-counting detector 304 (or other suitable computing device) and powered by the power source of the photon-counting detector 304 (or other power source, such as a power plug, cord, etc., of the C-arm imaging system 100). When activated, the motorized wheels 330, 332 roll along their respective track 314, 316 to translate the photon-counting detector 304 toward or away from (a portion of) the energy-integrating detector 302. More specifically, the energy-integrating detector 302 has a peripheral edge 334, and the photon-counting detector 304 has a peripheral edge 336. As shown in FIG. 5, the photon-counting detector 304 is in a first configuration, where the motorized wheels 330, 332 have contacted their respective mechanical stops 322, and where the axial axis 310 intersects both the energy-integrating detector 302 and the photon-counting detector 304.

Figure 6:
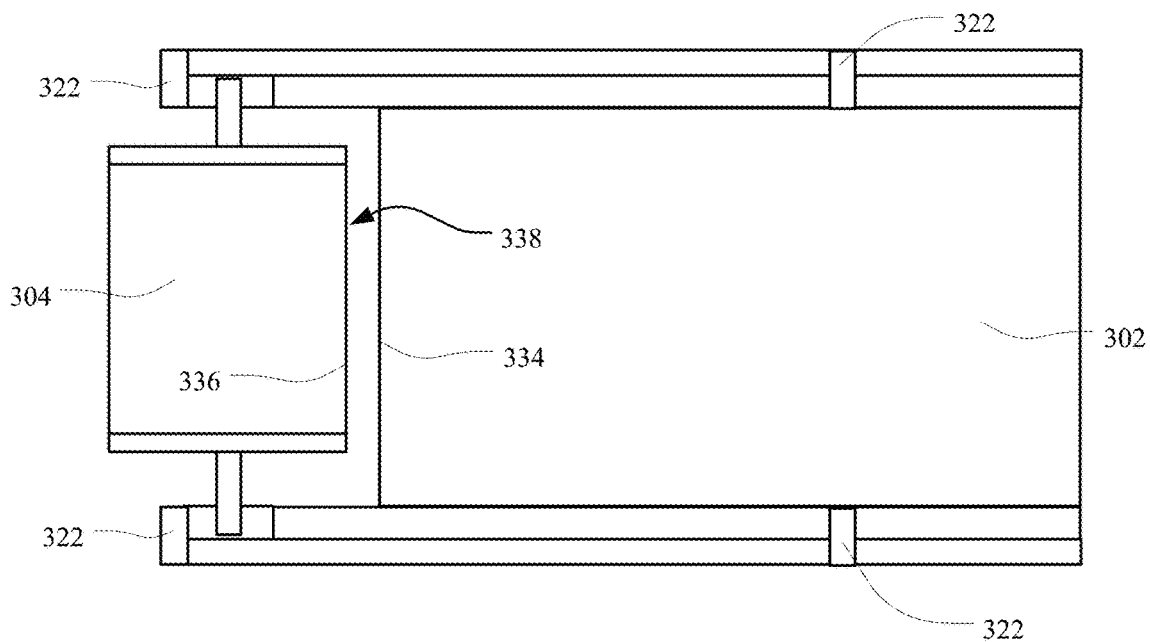
FIG. 6 is a bottom view of the photon-counting detector of the changeable x-ray detector system of FIG. 4 in a second configuration.

FIG. 6 shows the photon-counting detector 304 in a second configuration, where the motorized wheels 330, 332 have contacted the other respective mechanical stops 322. As shown, in this second configuration, a transverse gap 338 (e.g., transverse to the axial axis 310) is formed between the peripheral edges 334, 336 of the detectors 302, 304, and in particular, the transverse gap 338 separates respective surfaces of the detectors 302, 304. As described above, a suitable computing device can instruct the motorized wheels 330, 332 to roll along their respective tracks from the first configuration of FIG. 5 to the second configuration in FIG. 6, for example when the energy-integrated detector 302 is desired to be used to image a subject. Then, the suitable computing device can instruct the motorized wheels 330, 332 to roll along their respective track from the configuration of FIG. 6 to the configuration of FIG. 5, for example when the photon-counting detector 304 is desired to be used to image a subject.

In some non-limiting examples, and as shown in FIG. 4 an axial gap 340 separates the energy-integrating detector 302 from the photon-counting detector 304. This allows the photon-counting detector 304 to be easily translated relative to the energy-integrating detector 302. Additionally, as shown in FIGS. 4-6 the perimeter and sensing surface (e.g., the size of the x-ray sensing array) of the photon-counting detector 304 is smaller than the perimeter and sensing surface e.g., the size of the x-ray sensing array) of the energy-integrating detector 302. This decrease in size of the photon-counting detector 304 can be particularly advantageous. For example, the cost of the photon-counting detector 304 is significantly reduced, due to decreased size of the photon-counting detector 304. As another example, and as described above, by having a smaller photon-counting detector 304, the computational requirements are significantly reduced, which can be particularly helpful in the interventional radiology suite so that the images can be displayed and analyzed in real-time so that the practitioner can conduct the procedure without having to wait for acquisition (or rendering) time.

Figure 7:
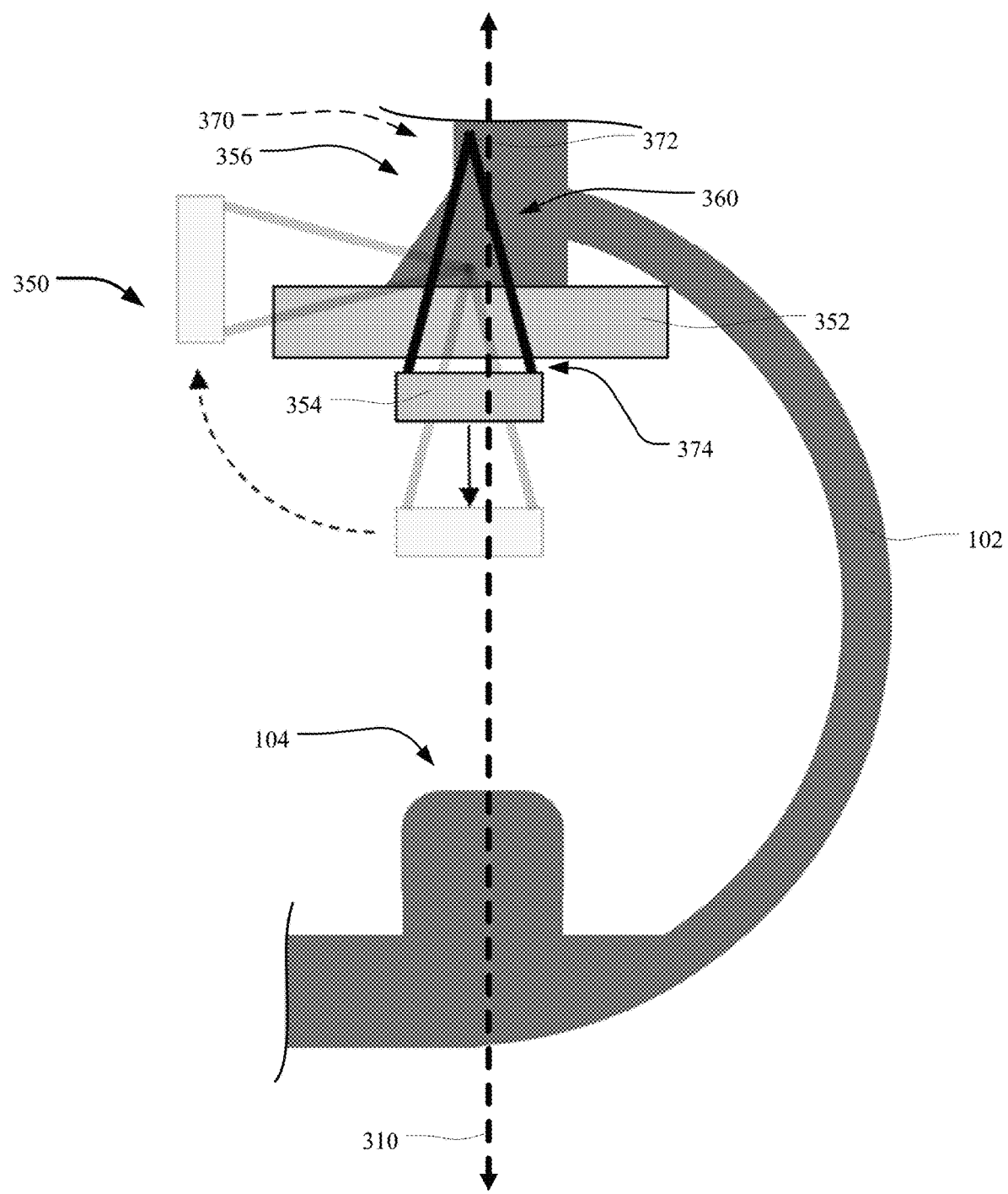
FIG. 7 is an illustration of another example of a changeable x-ray detector system integrated with and coupled to the C-arm of the C-arm x-ray imaging system of FIG. 1.
Figure 8:
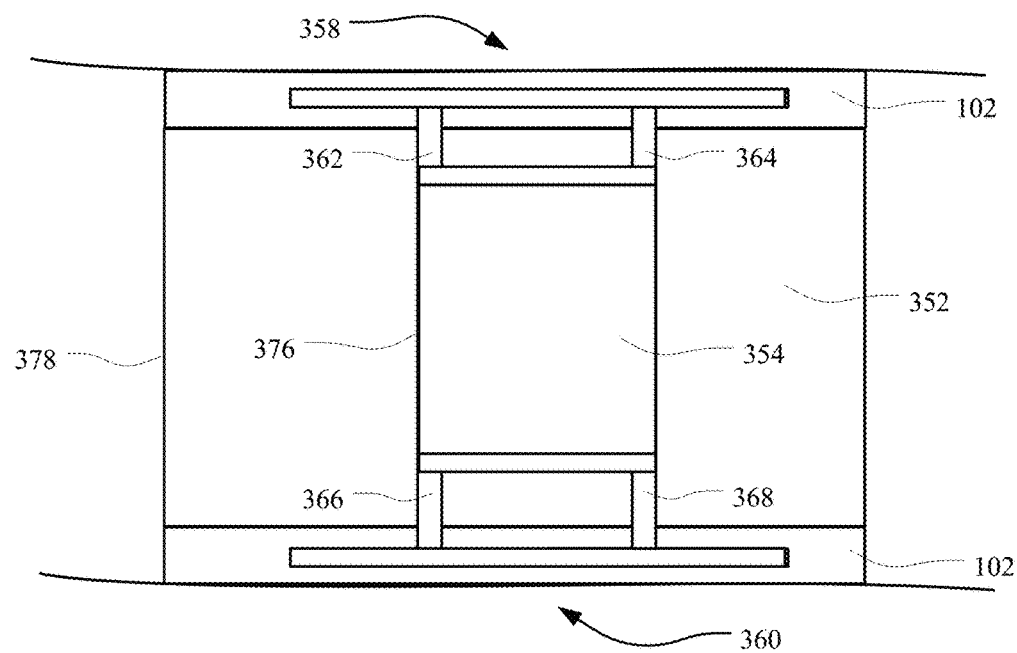
FIG. 8 is a bottom view of the photon-counting detector of the changeable x-ray detector system of FIG. 7 in a first configuration.

FIGS. 7 and 8 show another example of a changeable x-ray detector system 350 coupled and integrated with the C-arm x-ray imaging system 100. The changeable x-ray detector system 350 includes an energy-integrating detector 352 that is fixed to an end of the C-arm 102, a photon-counting detector 354, and a mounting system 356. As shown, the changeable x-ray detector system 300 is coupled to an end of the C-arm 102 opposite the x-ray source assembly 104. The x-ray source assembly 104 is configured to emit x-rays towards the changeable x-ray detector system 300 along a path that extends to define an axial axis 310. The mounting system 356 is pivotable between a first configuration in which the photon-counting detector 354 is situated in front of the energy-integrating detector 352 towards the x-ray source assembly 104 (and intersecting the axial axis 310), to a second configuration in which the photon-counting detector 354 is moved away from the energy-integrating detector 352 (and not intersecting the axial axis 310). As shown in FIG. 7, in the second configuration the detection surface of the photon-counting detector 354 is substantially (e.g., deviating by no more than 10°) parallel to the axial axis 310. Although not shown, it can be appreciated that there can be a number of intermediate positions that the mounting system 356 can have between the first and second configuration.

In some non-limiting examples, the mounting system 356 includes two support structures 358, 360 each of which is coupled to the housing of the photon-counting detector 354 at one end, and pivotally coupled to the end of the C-arm 102 at the opposite end. As shown, the support beams 358, 360 have a triangular shape that emanates at the pivotal location and extends radially outward until reaching the opposing end, which is coupled to the photon-counting detector 354. Each of the support structures 358, 360 are coupled to opposing ends of the photon-counting detector 354. In some configurations, the support structures 358, 360 can have a rhombus shape (or other shapes) each of which emanates from the pivotal location, extends radially outward, and then extends radially inward to retract as a single point (or mounting location). In some non-limiting examples, the support structure 358 has transverse beams 362, 364 (e.g., transverse to the axial axis 310) that extend and are coupled to one end of the photon-counting detector 354. Similarly, the mounting structure 360 also has transverse beams 366, 368 (e.g., transverse to the axial axis 310) that extend and are coupled to the second end (opposite the one end) of the photon-counting detector 354. The transverse beams 362, 364, 366, 368 can be particularly helpful if the photon-counting detector 354, such as illustrated, has a smaller dimension (e.g., width) than the energy-integrating detector 352. This allows the photon-counting detector 354 to be supported (and suspended) from the C-arm 102.

The support structures 358, 360, as described previously, also each include a pivotal connector 370, 372, respectively. The pivotal connector 370 of the support structure 358 pivotally couples the end of the support structure 358 (opposite the photon-counting detector 354) to the C-arm 102. Similarly, the pivotal connector 372 of the support structure 360 pivotally couples the end of the support structure 360 (opposite the photon-counting detector 354) to the C-arm 102. In some non-limiting examples, each of the pivotal connectors 370, 372 can include electric motors (and gears as appropriate) to drive rotation of the respective support structures 358, 360 and thereby driving rotation of the photon-counting detector 354. In some cases, an axial gap 374 that separates the energy-integrating detector 352 from the photon-counting detector 354 is desired to be minimized (e.g., to accommodate various sized subjects), or the pivotal clearance of the support structure 358, 360 is inadequate (e.g., the photon-counting detector 354 may contact the energy-integrating detector 352). So, each of the pivotal connectors 370, 372 can be configured to be translated axially (e.g., by a pulley system, a gear system with locks, a linear actuator system, etc.) prior to or after rotation via the pivotal connectors 370, 372 as appropriate.

Figure 9:
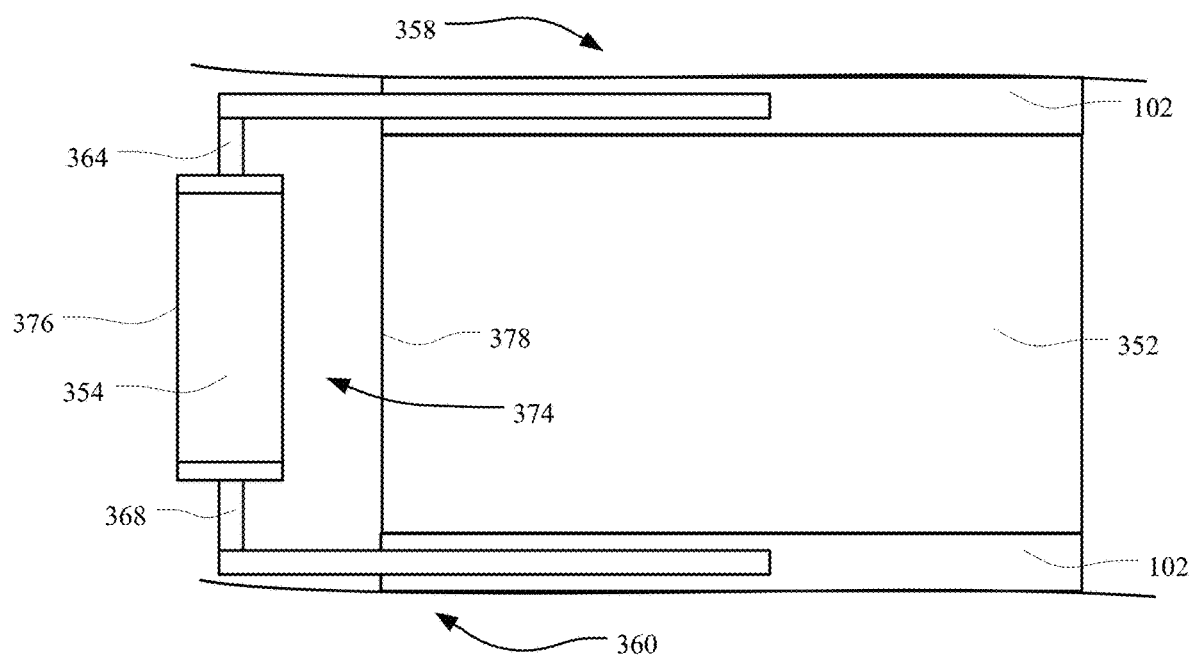
FIG. 9 is a bottom view of the photon-counting detector of the changeable x-ray detector system of FIG. 7 in a second configuration.

FIG. 8 shows the photon-counting detector 354 in a first configuration, where the support structures 358, 360 support and position the photon-counting detector 354 so that the axial axis 310 intersects both the photon-counting detector 354, and the energy-integrating detector 352. FIG. 9 shows the photon counting detector 354 in a second configuration, where a transverse gap 374 (e.g., transverse relative to the axial axis 310) is formed between a peripheral edge 376 of the photon counting detector 354, and a peripheral edge 378 of the energy-integrating detector 352. In some cases, the photon-counting detector 354 is configured to move from the first configuration to the second configuration by first translating the support structures 358, 360 (e.g., via the pivotal connectors) downwardly along the axial axis 310 and towards the x-ray source assembly 104. This can provide the support structures 358, 360 with the proper pivotal clearance. Then, the photon-counting detector 354 can be pivoted in a clockwise direction (e.g., relative to the view in FIG. 7), for example, by activation of the electrical motors that interface with the pivotal connectors 370, 372 using an appropriate computing device. This procedure can be utilized when the energy-integrating detector 352 is desired to be used for imaging a subject (e.g., to prevent blockage of x-rays from the x-ray source assembly 104 by the photon-counting detector 354). This process can be repeated in the opposing steps (e.g., rotating the support structures in the opposite direction, and translating the support structures upwardly after) to position the photon-counting detector 354 is the first configuration. Similarly to the changeable x-ray detector system 300, it can be appreciated that the changeable x-ray detector system 350 can be positioned in a number of intermediate configurations between the first and second configurations.

Figure 10:
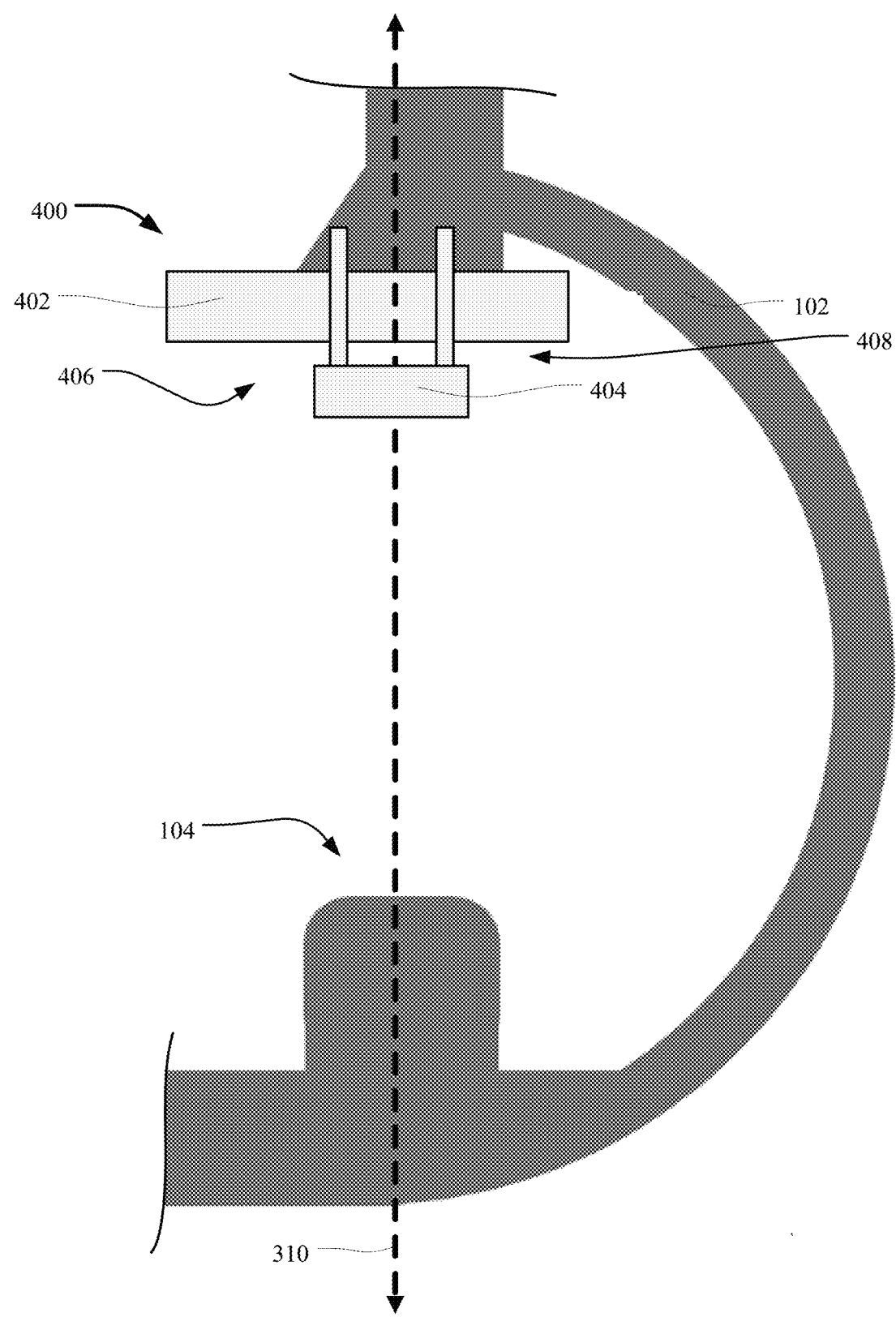
FIG. 10 is an illustration of another example of a changeable x-ray detector system integrated with and coupled to the C-arm of the C-arm x-ray imaging system of FIG. 1.
Figure 11:
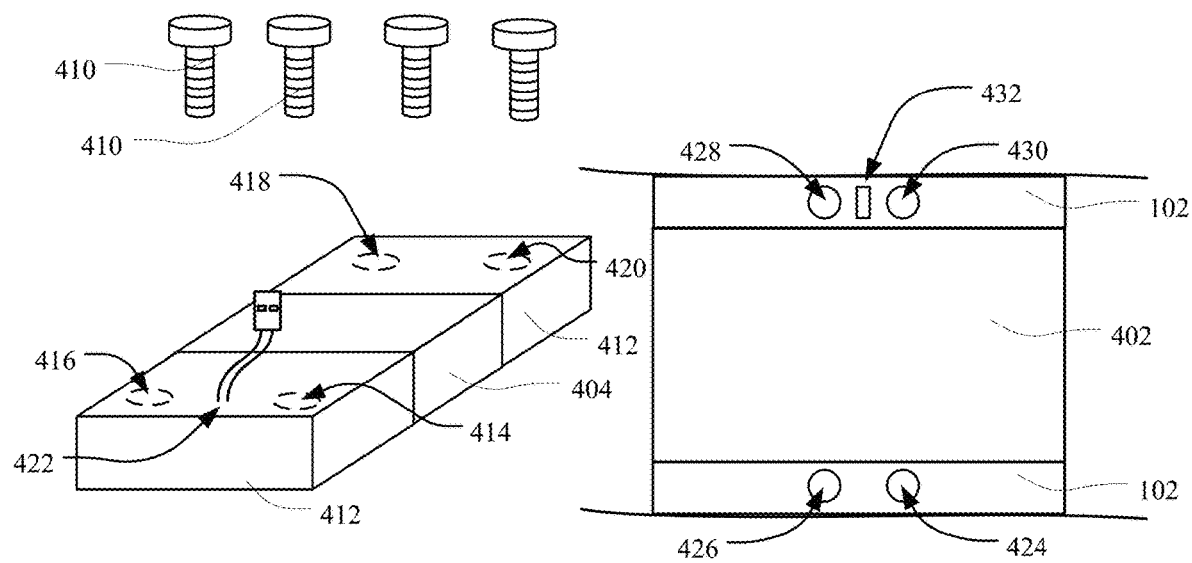
FIG. 11 is an illustration of a removably coupled photon-counting detector and a mounting system used to couple the photon-counting detector to the C-arm of the C-arm x-ray imaging system of FIG. 1.

FIGS. 10 and 11 shows an example of a changeable x-ray detector system 400 coupled to and integrated with the C-arm x-ray imaging system 100. The changeable x-ray detector system 400 includes an energy-integrating detector 402 that is fixed to an end of the C-arm 102, a photon-counting detector 304, and a mounting system 306. As shown, the changeable x-ray detector system 400 is coupled to an end of the C-arm 102 opposite the x-ray source assembly 104. The x-ray source assembly 104 is configured to emit x-rays towards the changeable x-ray detector system 300 along a path that extends to define an axial axis 310. The mounting system 406 allows the photon-counting detector 404 to be removably coupled to the end of the C-arm 102 opposite the x-ray source assembly 104. In the coupled configuration, such as in the illustrated configuration of FIG. 10, the mounting system 406 is coupled to the end of the C-arm 102 and supports the photon-counting detector 404 relative to the C-arm 102. In this configuration, the photon-counting detector 404 is positioned in front of the energy-integrating detector 402 towards the x-ray source assembly 104 along the axial axis 310. In some configurations, such as illustrated, an axial gap 408 separates the photon-counting detector 404 from the energy integrating detector 402. Although in some configurations, when the photon-counting detector 404 is coupled to the C-arm 102, the photon-counting detector 404 can be flush with the energy-integrating detector 402.

In some non-limiting examples, the mounting system 406 includes a number of fasteners 410 implemented as threaded bolts that can allow the photon-counting detector 404 to be removably coupled to the C-arm 102. In particular, the photon-counting detector 404 includes a housing 412 having a number of threaded bores 414, 416, 418, 420 each configured to receive and threadingly engage with a corresponding fastener 410. In some configurations, such as when the photon counting detector 404 does not include other circuitry other than the detector array (e.g., communication systems, processors, memory, etc.), the photon-counting detector 404 can include an electrical connector 422.

As also shown in FIG. 11 the C-arm 102 also includes a number of mounting locations implemented also as threaded bores 424, 426, 428, 430 that are also each configured to threadingly engage with a corresponding fastener 410 to couple the photon-counting detector 404 to the C-arm 102. In some configurations, such as when the photon-counting detector 404 is implemented with an electrical connector 422, the C-arm 102 can include an electrical port 432 that receives and electrically connects the electrical connector 422 to the C-arm x-ray system 100 (including the electrical systems therein). This can allow the photon-counting detector 404 to leverage the already existing systems of the C-arm x-ray system 100, such as, for example, the DAS 144 and to allow the systems of the C-arm x-ray system 100 to be electrically connected to and readily control the photon-counting detector 404. In some non-limiting examples, the C-arm x-ray system 100 can determine that the electrical connector 422 has been connected to the electrical port 432, and can accordingly instruct the DAS 144 to acquire data from the photon-counting detector 404 rather than the energy-integrating detector 404.

Figure 12:
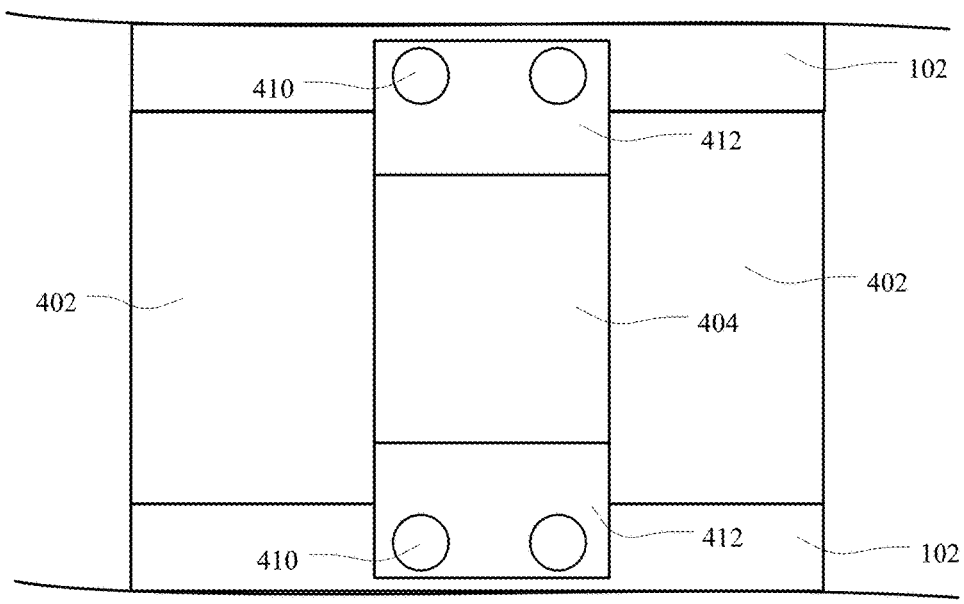
FIG. 12 is a bottom view of the removably coupled photon-counting detector of FIG. 11 coupled to the C-arm of the C-arm x-ray imaging system of FIG. 1.

FIG. 12 shows the photon-counting detector 404 coupled to the end of the C-arm 102. When the photon-counting detector 404 is desired to be used for imaging (rather than the energy-integrated detector 402), a user can install the each of the fasteners 410 through the respective bore 414, 416, 418, 420 of the housing 412 of the photon-counting detector 404 and through the respective bore 424, 426, 428, 430 of the end of the C-arm 102. Then, after the practitioner has completed using the photon-counting detector 404, a user can uninstall each of the fasteners 410 to remove the photon-counting detector 404 from the end of the C-arm 102 (or otherwise decouple the photon-counting detector 404 from the C-arm 102).

Figure 13:
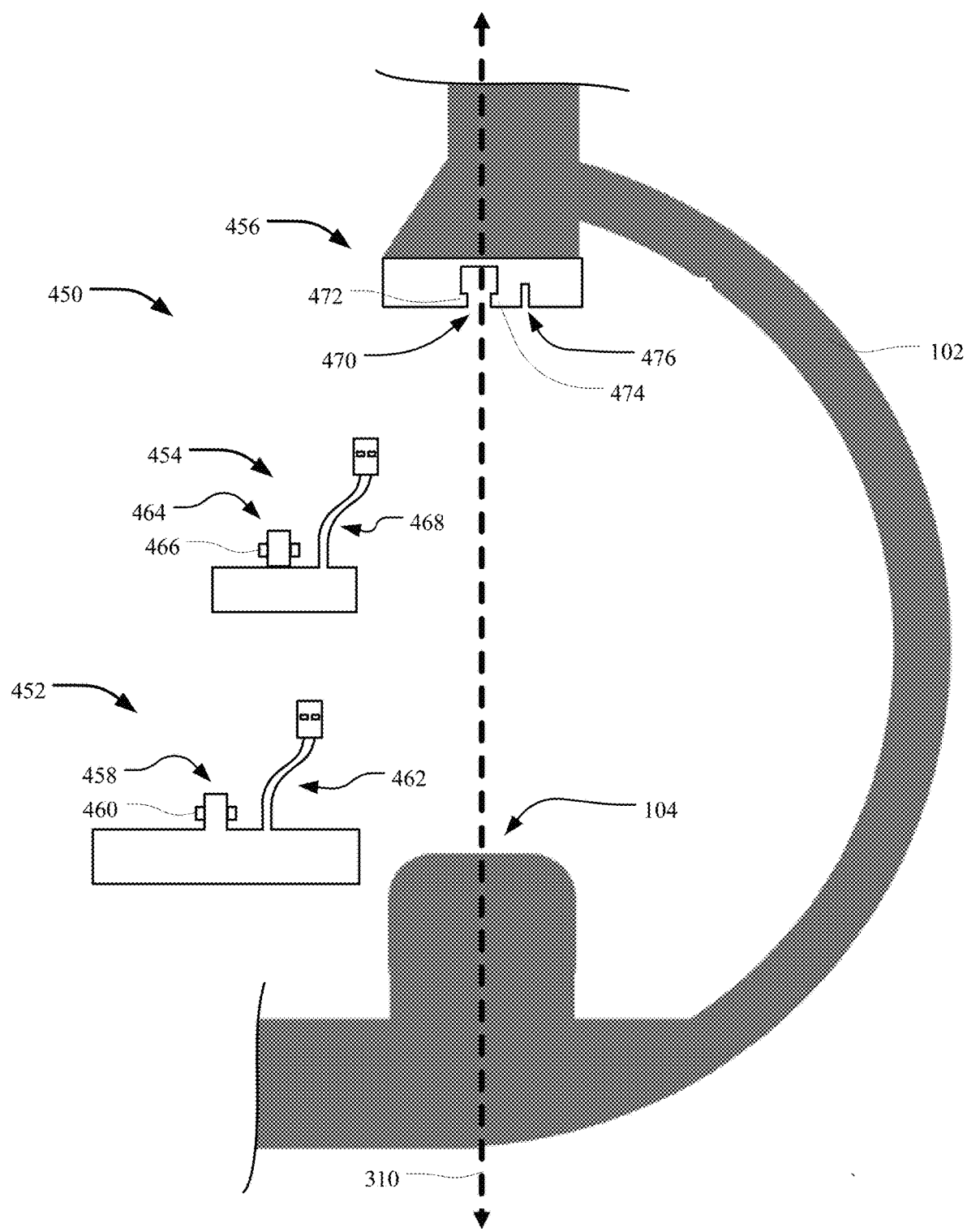
FIG. 13 is an illustration of another example of a changeable x-ray detector system integrated with and coupled to the C-arm of the C-arm x-ray imaging system of FIG. 1.

FIG. 13 shows an example of a changeable x-ray detector system 450 coupled to and integrated with the C-arm x-ray imaging system 100. The changeable x-ray detector system 450 includes an energy-integrating detector 452, a photon-counting detector 454, and a mounting system 456. The energy-integrating detector 452 includes a mounting protrusion 458 having a snap-clip 460. The snap-clip 460 can be typically structured and generally allows the mounting protrusion 458 to be secured to a mounting structure in one configuration, and to be unsecured to the mounting structure in a second configuration (e.g., decoupled, such as the snap-clip 460 retracting). Additionally, in some cases, such as when the energy-integrating detector 452 does not have additional circuitry other than the detector array (e.g., communication systems, processors, memory, etc.). the energy-integrating detector 452 can have an electrical connector 462 that can allow the C-arm x-ray imaging system 100 to utilize the energy-integrating detector 452.

Similarly, the photon-counting detector 454 also includes a mounting protrusion 464 having a snap-clip 466. The snap-clip 466 can be typically structured and generally allows the mounting protrusion 464 to be secured to a mounting structure in one configuration, and to be unsecured to the mounting structure in a second configuration (e.g., decoupled, such as the snap-clip 466 retracting). Additionally, in some cases, such as when the photon-counting detector 454 does not have additional circuitry other than the detector array (e.g., communication systems, processors, memory, etc.). The photon-counting detector 454 can have an electrical connector 468 that can allow the C-arm x-ray imaging system 100 to utilize the photon-counting detector 454.

As shown, the mounting system 456 includes a mounting socket 470 having transverse protrusions 472, 474 that extend towards the axial axis 310. In some configurations, such as where the energy-integrating detector 452, or the photon-counting detector 454, or both, include electrical connectors (e.g., the detectors 452, 454, or both, not having circuitry other than the detector array), the mounting system 456 can include an electrical port 476 that receives and electrically connects either of the electrical connectors 462, 468 to the C-arm x-ray imaging system 100. Similarly to the changeable x-ray system 400, when the electrical connector is interfaced with the electrical port, the C-arm x-ray imaging system 100 is electrically connected to control and receive data from the respective detector. In some non-limiting examples, although not shown, the electrical connectors 462, 468 can be received within a bore of the respective mounting protrusion 458, 464, and correspondingly, the electrical port 476 can be situated within the mounting socket 470. This configuration can prevent the need for additional holes (or sockets), and can prevent unwanted bending or issues within compressing the chord of the electrical connectors 462, 468 when one of the electrical connectors is received in the electrical port.

As shown, the photon-counting detector 454 has a smaller spatial footprint than the energy-integrating detector 452. In particular, the sensing surface of the photon-counting detector 454 (e.g., the array of x-ray sensing elements of the photon-counting detector 454) is smaller (e.g., has a smaller area) than the sensing surface of the energy-integrating detector 454. Additionally, the width, the length, or both of the photon-counting detector 454 is smaller than the energy-integrating detector 454. In the illustrated non-limiting example, the photon-counting detector 454 has a smaller area and has a smaller width than the energy-integrating detector 452.

Figure 14:
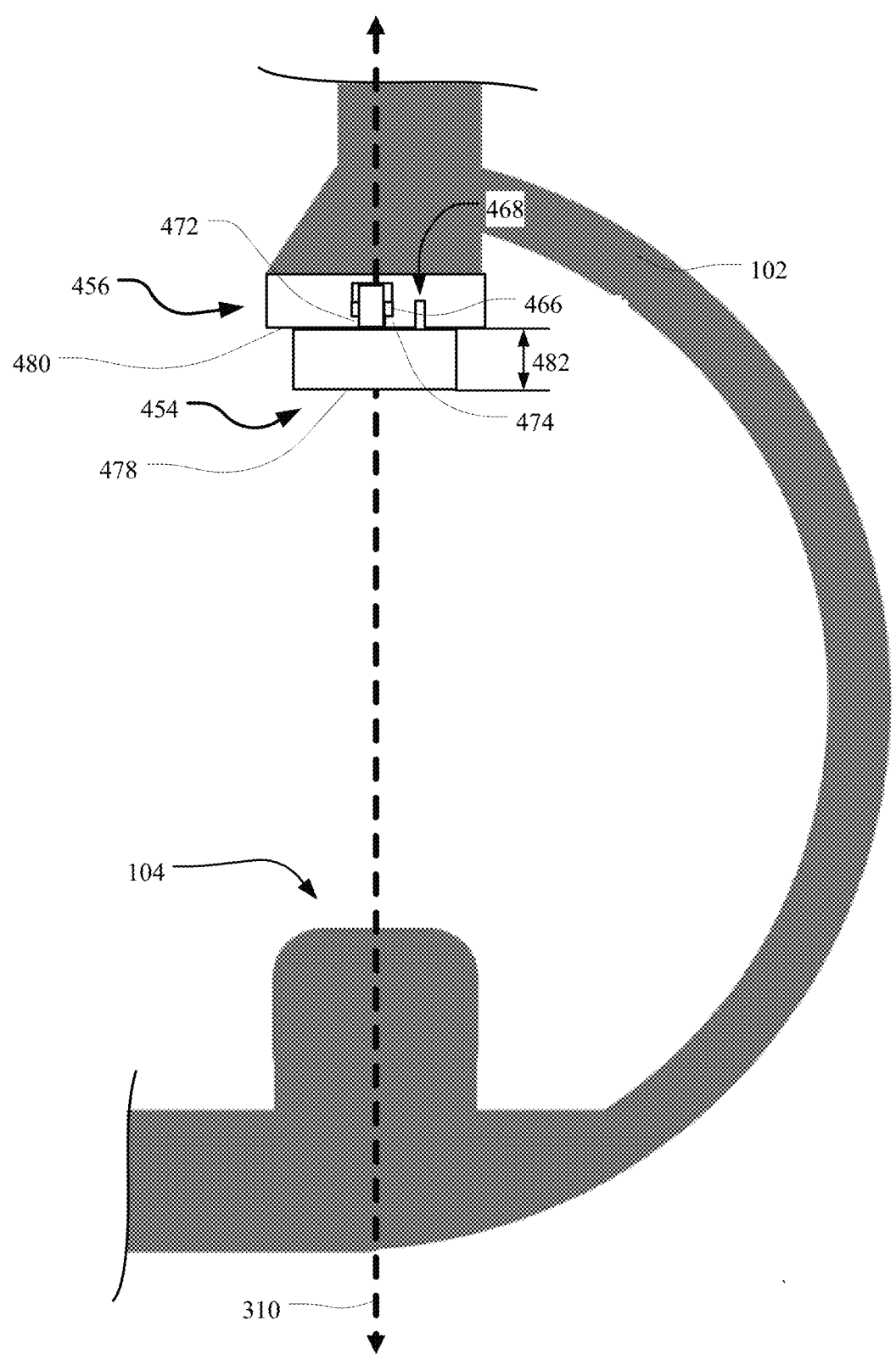
FIG. 14 is the photon-counting detector of the changeable x-ray detector system of FIG. 13 coupled to the mounting system positioned on the end of the C-arm.
Figure 15:
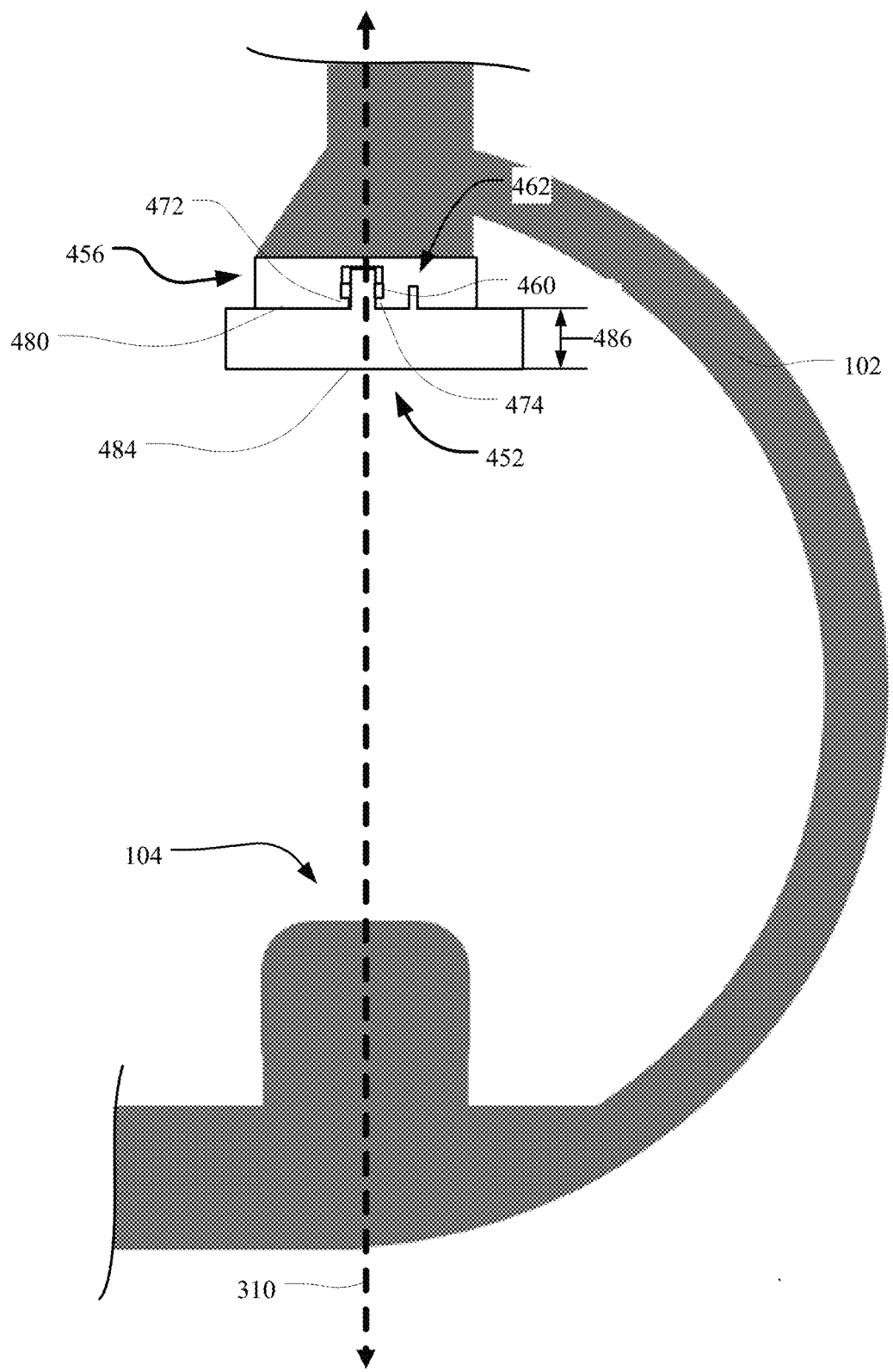
FIG. 15 is the energy-integrated detector of the changeable x-ray detector system of FIG. 13 coupled to the mounting system positioned on the end of the C-arm.

FIGS. 14 and 15 show the photon-counting detector 454 coupled to the mounting system 456, and the energy-integrating detector 452 coupled to the mounting system 456, respectively. As shown in FIG. 14, the mounting protrusion 464 has been inserted into the mounting socket 470, the electrical connector 468 has been inserted and electrically connected to the electrical port 476, and the snap-clip 466 has retracted to block downward translation of the photon-counting detector 454 along the axial axis 310 towards the x-ray source assembly 104 (e.g., by abutting against the transverse protrusions 472, 474). Similarly, the upper surface of the mounting protrusion 464 is in contact with the upper surface of the mounting socket 470, which can prevent translation of the photon-counting detector 454 along the axial axis 310 away from the x-ray source assembly 104. Blocking both directions of translation can provide a reliable position between the photon counting detector 454 and the mounting system 456.

As shown in FIG. 15, the mounting protrusion 458 has been inserted into the mounting socket 470, the electrical connector 462 has been inserted and electrically connected to the electrical port 476, and the snap-clip 460 has retracted to block translation of the energy-integrated detector 452. Similarly to the photon-counting detector 454, when the energy-integrating detector 452 is coupled to the mounting system 456, axial translation along the axial axis 310 is blocked in both directions to provide a reliable position between the energy-integrating detector 454 and the mounting system 456.

In some configurations, and as shown, the axial thickness of both the energy-integrating detector 452 and the photon-counting detector 454 is substantially identical (e.g., deviating by less than 10%). In particular, a surface 478 of the photon-counting detector 454 and a surface 480 of the mounting system 456 define an axial distance 482 (e.g., along the axial axis 310). Similarly, a surface 484 of the energy-integrating detector 452 and the surface 480 of the mounting system 456 define an axial distance 486 (e.g., along the axial axis 310). The axial distances 482, 486 are substantially similar. Stated another way, the axial distance between the x-ray source assembly 104 and the surface 478 of the photon-counting detector 454 when installed, and the axial distance between the x-ray source assembly 104 and the energy-integrating detector 452 when installed is substantially identical. The axial distances being substantially similar to each other can prevent the need for extensive calibration implementations when the detectors are switched (e.g., based on the desired imaging procedure) as the distance the x-rays have to travel from the x-ray source assembly 104 to being detected by the detector is substantially identical between the two detectors.

The changeable x-ray detector system 450 as illustrated in FIGS. 13-15 allows one detector to be installed and used, while the other detector is not used. In particular, the changeable x-ray detector system 450 has the energy-integrating detector 452 that is configured to be removably coupled to a mounting system 456 at one end of the C-arm 102 (e.g., opposite the x-ray source assembly 104), and the photon-counting detector 454 that is also configured to be removably coupled to the mounting system 456. When one of the detectors 452, 454 is installed the C-arm imaging system 100 utilizes the installed detector 452, 454 and does not utilize, or in other words, does not image with the other detector 452, 454. Although the changeable x-ray detector system 450 has been described with the mounting socket 470 and the mounting protrusions 458, 464, in other non-limiting examples other removably coupled configurations can be utilized, which can include, for example, fastener assemblies (e.g., bolts and threaded holes), brackets, etc.

Figure 16:
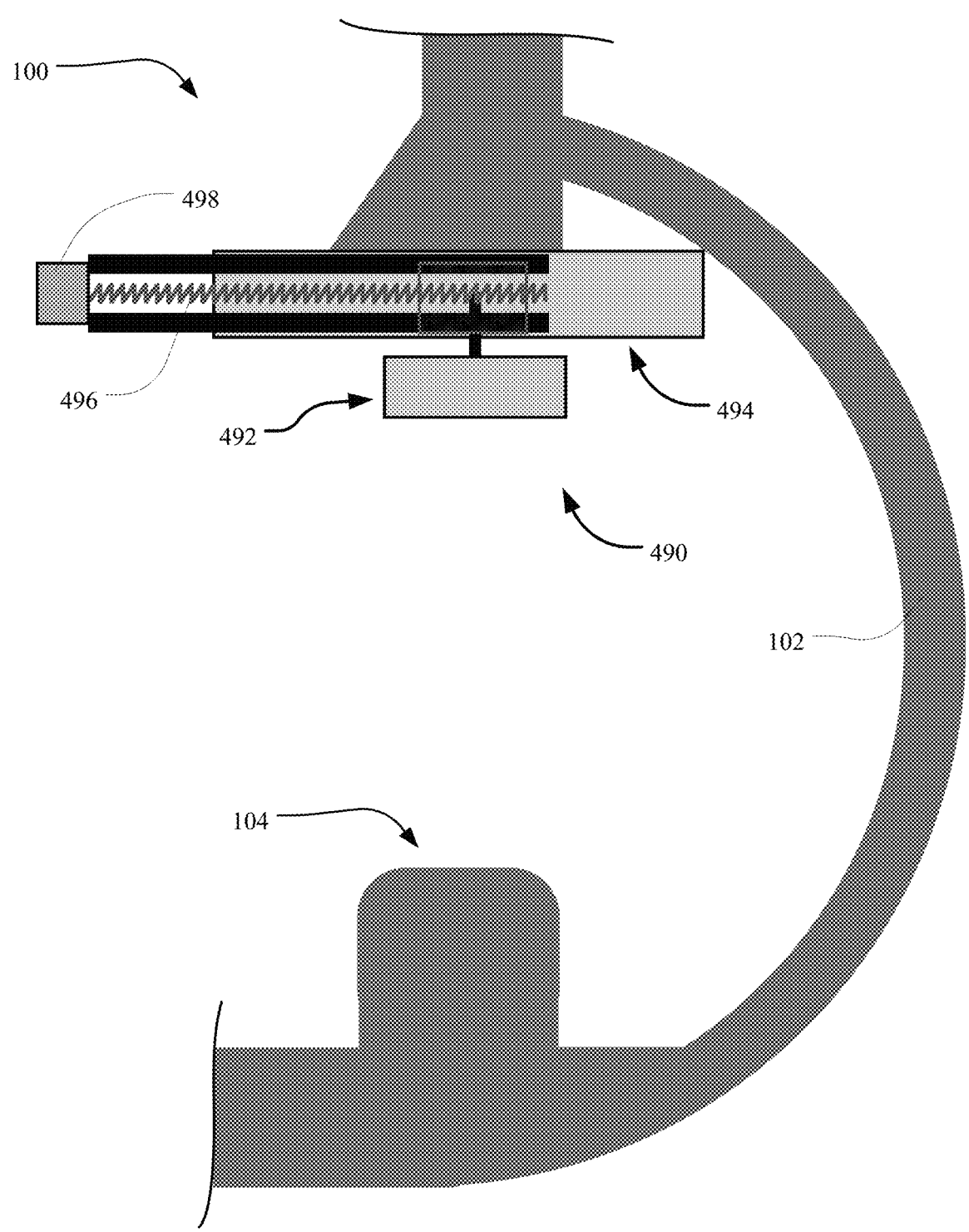
FIG. 16 is an illustration of a further example of a changeable x-ray detector system integrated with and coupled to the C-arm of the C-arm x-ray imaging system of FIG. 1.

FIG. 16 shows a further example of a changeable x-ray detector system 490 coupled to and integrated with the C-arm x-ray imaging system 100. The changeable x-ray detector system 490 includes a photon counting detector 492 mounted below an energy-integrating or flat panel detector 494 and both supported on the c-arm gantry 102 to receive x-rays from the x-ray source assembly 104. The changeable x-ray detector system 490 includes an actuation system 494 that, as illustrated, includes a translation system 496 that facilitates moving the photon counting detector 492 to be positioned in front of the energy integrating detector 494, as illustrated, and moved along the translation system 496 to not obscure the energy integrating detector 494 and allow it to acquire the x-rays from the x-ray source 104. The translation system 496 may include a linear actuator. The learn actuator may be a screw drive or other mechanical drive system. The translation system 496 may be driven by a motor 498.

Figure 17:
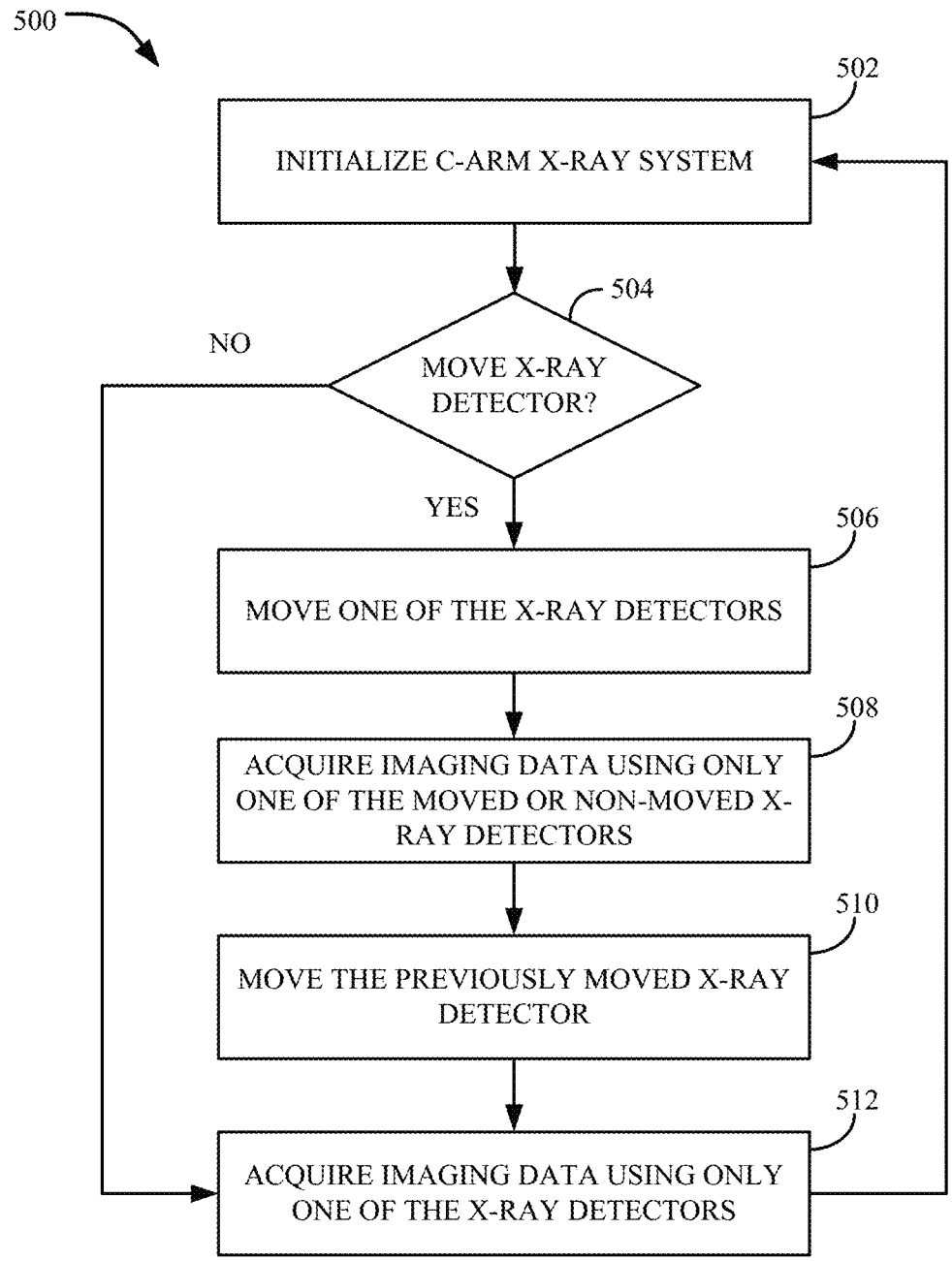
FIG. 17 is a flowchart of a process for controlling a C-arm x-ray imaging system.

FIG. 17 shows a flowchart of a process 500 for controlling a C-arm x-ray imaging system. In some non-limiting examples, appropriate steps within process 500 can be implemented using a suitable computing device (e.g., the processor of the operator workstation 122), as appropriate. At 502, process 500 includes initialize the c-arm x-ray imaging system (e.g., the C-arm x-ray imaging system 100). In some non-limiting examples, initializing the c-arm x-ray imaging system can ensure that electrical connections (or communications) are working appropriately. For example, the c-arm x-ray imaging system can communicate with one or both of the detectors to ensure that imaging data can be acquired from the detector(s). In some cases, initializing the C-arm x-ray system can include the practitioner (e.g., the interventional radiologist) interacting and selecting a desired imaging procedure on the operating system of the computing device (e.g., the operator workstation 122), which when selected transmits a user input so that the C-arm receives the user input indicating the selected imaging procedure. In some configurations, specific imaging procedures are tied to particular detectors. For example, a fluoroscopy acquisition or a cone beam computed tomography acquisition can be tied to the energy-integrated detector, while a high quality computed tomography acquisition for hemorrhage analysis, assessment of a particular vessel or thrombus, or metal artifact reduction can be tied to the photon-counting detector.

At 504, process 500 determines whether or not to move the x-ray detector. In some cases, the user input received by the C-arm x-ray imaging system can be compared to a current position (and identity) of one of the x-ray detectors. For example, with the user input being tied to the energy-integrated detector, and the photon-counting detector is in a position to receive x-rays from the x-ray source assembly, while the energy-integrating detector is not in a position to receive x-rays from the x-ray source assembly (e.g., the photon-counting detector is blocking the energy-integrating detector) process 500 can determine that the photon-counting detector should be moved. In other cases, with the user input being tied to the photon-counting detector, and the photon-counting detector is in a position to receive x-rays from the x-ray source assembly, while the energy-integrating detector is not in a position to receive x-rays from the x-ray source assembly, process 500 can determine that the photon-counting detector does not need to be moved. In other cases, the practitioner can instruct the C-arm to move (or not to move) the particular x-ray detector (e.g., the energy-integrated detector, or the photon-counting detector), where the C-arm receives a user input indicative of moving or not moving the particular x-ray detector. The position sensing ability can be implemented in many different ways. For example, in some configurations, position sensors (e.g., hall-effect sensors, optical sensors, etc.) can be coupled to specific locations of the mounting system (e.g., the mechanical stops) and can be in communication with the C-arm x-ray imaging system to determine that the particular x-ray detector is at a particular location.

If process 500 determines at 502 that the particular x-ray detector should move, process 500 can proceed to 506 of process 500 which can include move one of the x-ray detectors. Moving one of the x-ray detectors can include causing the activation of electrical motor(s) to pivot about a pivoting location, to roll along a track in a direction, to extend (or retract) linear actuators, all of which can move, or more specifically translate the one of the x-ray detectors out of the path that is defined by x-rays being emitted from the x-ray source assembly. In some configurations, moving the x-ray detector can include decoupling the one of the x-ray detectors (e.g., the photon-counting detector 404) from the end of the C-arm. In some configurations, after the x-ray detector has been decoupled, the other x-ray detector can be recoupled to the end of the C-arm (e.g., one of the detectors 452, 454). In some non-limiting examples, after the desired detector has been moved into position, the desired detector can be calibrated prior to acquiring imaging data.

If process 500 determines at 502 that the particular x-ray detector should not move process 500 can proceed to 512 of process 500 which can include acquire imaging data using only one of the x-ray detectors. For example, in some cases, if the photon-counting x-ray detector is positioned in front of the energy-integrating x-ray detector and the photon-counting x-ray detector is the detector to be used to image the subject, the C-arm x-ray imaging system can acquire imaging data using only the photon-counting x-ray detector (and not acquiring imaging data using the energy-integrating detector at that specific time). At 512 process 500 can also include, aside from acquiring imaging data from the x-ray detector, forming (or constructing) an image using the acquired imaging data, and presenting the formed image on a display (e.g., so that the practitioner can view the presented image). In some non-limiting examples, the detector to be imaged with can be calibrated prior to acquiring imaging data.

At 508, process 500 can include acquire imaging data using only one of the moved x-ray detector or the unmoved (or non-moved) x-ray detector (e.g., not acquiring imaging data using both of the detectors at the same time). In some cases, the moved x-ray detector is moved out of the path of the x-rays, or in other cases, the x-ray detector is moved into the path of the x-rays. Acquiring imaging data at 508 of process 500 can also include forming an image, and presenting the image on the display.

At 510, process 500 can include move the previously moved x-ray detector. In some cases, the previously moved x-ray detector is moved out of the path of the x-rays, or in other cases, the previously moved x-ray detector is moved into the path of the x-rays. Once sufficiently moved, process 500 can proceed to 512 to acquire imaging data using only the other x-ray detector, different than the x-ray detector used to acquire image data at 508 of process 500 (e.g., and not acquiring imaging data using the x-ray detector used to acquire image data at 508). In some cases, this can involve decoupling the x-ray detector used to acquire imaging data at 508 of process 500, and recoupling the other x-ray detector to acquire imaging data. In some non-limiting examples, the detector to be imaged with can be calibrated prior to acquiring imaging data. At 512, once completed, process 500 can proceed back to 502 to initialize the c-arm x-ray system.

Figure 18:
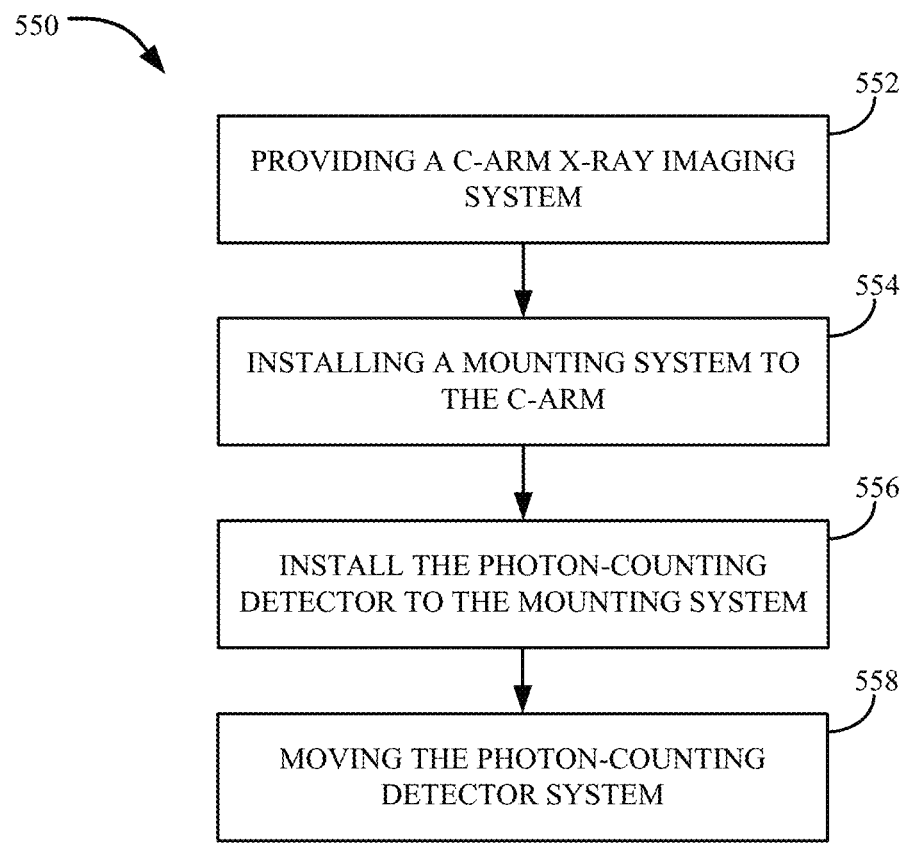
FIG. 18 is a flowchart of a process for retrofitting a C-arm x-ray imaging system.

FIG. 18 shows a flowchart of a process 550 for retrofitting a C-arm x-ray imaging system (e.g., the C-arm x-ray imaging system 100). At 552, process 500 includes providing a C-arm x-ray imaging system. In some non-limiting examples, the C-arm x-ray imaging system is a conventional C-arm x-ray imaging system having an energy-integrating x-ray detector of a specific size (e.g., a detection surface, a width, a length, etc.). At 554, process 550 can include installing a mounting system to the end of the C-arm (e.g., opposite the x-ray source assembly). In some non-limiting examples, the mounting system can be the rail system, the bracket system, the sockets, the fastening assemblies (e.g., fastening locations in the end of the C-arm), the telescoping system, the linear actuators, the pulley system, the belt system, etc.

At 556, process 500 can include installing the photon-counting detector to the mounting system. Depending on the implementation of the mounting system, installing the photon-counting detector to the mounting system can be achieved in different ways. For example, when the mounting system is the rail system (e.g., of FIG. 4) installing the photon-counting detector can include receiving and securing the motorized wheels to the respective tracks. As another example, when the mounting system includes fastening assemblies, the photon-counting detector can be coupled to the mounting system with fasteners.

At 558, process 500 can include moving the photon-counting detector system. In some cases, the energy-integrated detector can be preferred for some imaging procedures. So, the photon-counting detector can be translated away from the energy-integrated detector, so that the photon-counting detector does not block the energy-integrated detector. Similarly to the previous discussion, the spatial footprint of the photon-counting detector is smaller than the spatial footprint of the energy-integrated detector. For example, the energy-integrated detector can have a larger width, a larger length, and a larger sensing surface area, than the photon-counting detector. At 558, process 550 can also include most (or all) of the steps of process 500.

EXAMPLES

The following examples have been presented in order to further illustrate aspects of the disclosure, and are not meant to limit the scope of the disclosure in any way.

X-ray photon-counting detectors have been developed in past decades for various applications in medical imaging and material science. Compared to energy-integrating X-ray detectors working in a current mode, photon-counting detectors are operated in a pulse mode based on each single event, meaning that theoretically each x-ray photon interaction occurred within the detection material can be processed and registered individually. Full panel photon-counting detectors are significantly more expensive than conventional x-ray detectors, but allow for more precise measurements as they do not suffer from scattering and spreading of light photons (as shown below).

As shown below, a hybrid detector structure using a translatable semiconductor x-ray photon-counting detector (PCD) strip and a non-translatable scintillator-based flat panel detector (FPD) have been developed. Both detectors have been mounted on the C-arm gantry of the interventional x-ray system. The two detectors share the same x-ray tube. The FPD provides a much larger longitudinal spatial coverage and can be used in conventional two-dimensional imaging (e.g. fluoroscopy, DSA) and three-dimensional cone beam CT acquisitions. During these acquisitions, the PCD is moved out of the x-ray field so that it does not block the view of the FPD.

The advantages of PCD are threefold: first, it provides a much higher spatial resolution; second, it provides a much better iodine contrast-to-noise ratio due to more optimal signal weighting of x-ray photons; third, it provides multiple energy channels for every pixel to discriminate x-ray photons with different energies. All these features translate into high quality greyscale CT images with higher spatial resolution and better contrast-to-noise ratio and color-coded spectral CT images from a single acquisition. The quality of the greyscale CT images and spectral CT images are comparable to those of the state-of-the-art multi-detector row CT (MDCT) images, but the cost of the hybrid detector is orders of magnitude lower than that of installing a MDCT scanner in the interventional room.

Compared with a C-arm interventional x-ray system that completely replaces the scintillator FPD by a large area PCD, the cost of a narrower PCD strip is significantly reduced. The hybrid strategy allows a full spatial coverage without using an expensive large area PCD. For example, using a motorized translation motor, a user can easily switch between the two detectors based on the clinical imaging tasks. For example, for the selective removal of signal from iodine staining in the brain during a neurovascular interventional procedure, a physician can use the PCD to obtain a virtual non-contrast CT image the region with suspected iodine staining to assess intracranial hemorrhage. The spectral CT capability of PCD also helps to remove beam hardening artifacts from metallic clips and implants.

Although some of the discussion above is framed in particular around systems, such as the various isolation system, those of skill in the art will recognize therein an inherent disclosure of corresponding methods of use (or operation) of the disclosed systems, and the methods of installing the disclosed systems. Correspondingly, some non-limiting examples of the disclosure can include methods of using, making, and installing isolation systems.

Although the invention has been described and illustrated in the foregoing illustrative non-limiting examples, it is understood that the present disclosure has been made only by way of example, and that numerous changes in the details of implementation of the invention can be made without departing from the spirit and scope of the invention, which is limited only by the claims that follow. Features of the disclosed non-limiting examples can be combined and rearranged in various ways.

Furthermore, the non-limiting examples of the disclosure provided herein are not limited in application to the details of construction and the arrangement of components set forth in the following description or illustrated in the following drawings. The invention is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Also, the use the phraseology and terminology used herein is for the purpose of description and should not be regarded as limiting. The use of "right", "left", "front", "back", "upper", "lower", "above", "below", "top", or "bottom" and variations thereof herein is for the purpose of description and should not be regarded as limiting. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise specified or limited, phrases similar to "at least one of A, B, and C," "one or more of A, B, and C," etc., are meant to indicate A, or B, or C, or any combination of A, B, and/or C, including combinations with multiple or single instances of A, B, and/or C.

In some non-limiting examples, aspects of the present disclosure, including computerized implementations of methods, can be implemented as a system, method, apparatus, or article of manufacture using standard programming or engineering techniques to produce software, firmware, hardware, or any combination thereof to control a processor device, a computer (e.g., a processor device operatively coupled to a memory), or another electronically operated controller to implement aspects detailed herein. Accordingly, for example, non-limiting examples of the invention can be implemented as a set of instructions, tangibly embodied on a non-transitory computer-readable media, such that a processor device can implement the instructions based upon reading the instructions from the computer-readable media. Some non-limiting examples of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the invention. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," etc. are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, the term, "controller" and "processor" and "computer" include any device capable of executing a computer program, or any device that includes logic gates configured to execute the described functionality. For example, this may include a processor, a microcontroller, a field-programmable gate array, a programmable logic controller, etc. As another example, these terms may include one or more processors and memories and/or one or more programmable hardware elements, such as any of types of processors, CPUs, microcontrollers, digital signal processors, or other devices capable of executing software instructions.

The invention claimed is:

1. A C-arm x-ray imaging system comprising:
a gantry formed as a C-arm configured to pivot about a pivot axis;
an x-ray source coupled to a first end of the C-arm, the x-ray source configured to emit x-rays along a path extending to define an axial axis; and
a changeable x-ray detector system coupled to a second end of the C-arm arranged in the axial axis, the changeable x-ray detector system configured to receive x-rays emitted from the x-ray source along the path, the changeable x-ray detector system including:
an energy-integrating x-ray detector having an array of x-ray sensing elements that are configured to sense x-rays emitted from the x-ray source;
a photon-counting detector having another array of x-ray sensing elements configured to determine an interaction between individual x-ray photons from the x-ray source and individual sensing elements of the another array of x-ray sensing elements;
a mounting system configured to move at least one of the energy-integrating detector or the photon-counting detector between a first position in the path to receive the x-rays emitted from the x-ray source and a second position removed from the path to not receive the x-rays emitted from the x-ray source,
wherein only one of the energy-integrating detector and the photon-counting detector is configured to receive the x-rays emitted from the x-ray source at a time.

2. The C-arm x-ray imaging system of claim 1, wherein mounting system includes one of a hinge, a rail system, a bracket system, or a socket to secure the at least one of the energy-integrating detector or the photon-counting detector in the first position in the path to receive the x-rays emitted from the x-ray source.

3. The C-arm x-ray imaging system of claim 1, wherein the mounting system translates the photon-counting detector in a direction substantially perpendicular to the axial axis into the second position.

4. The C-arm x-ray imaging system of claim 3, wherein the array of x-ray sensing elements of the energy-integrating x-ray detector defines a first sensing area having a peripheral edge,
wherein the another array of x-ray sensing elements of the photon-counting detector defines a second sensing area,
wherein the first sensing area is substantially parallel to the second sensing area, and
wherein the photon-counting detector is configured to move from the second position to the first position, such that in moving from the first position to the second position, the entire first sensing area is clearing and being positioned away from the peripheral edge of the first sensing area.

5. The C-arm x-ray imaging system of claim 4, wherein in the first configuration a gap is defined between the peripheral edge of the first sensing area, and another peripheral edge of the second sensing area.

6. The C-arm x-ray imaging system of claim 4, wherein the first sensing area is larger than the second sensing area.

7. The C-arm x-ray imaging system of claim 4, wherein individual x-ray sensor elements of the energy-integrating x-ray detector are larger than individual x-ray sensing elements of the photon-counting detector.

8. The C-arm x-ray imaging system of claim 4, further comprising a mounting structure that is coupled to and secures the changeable x-ray detector assembly to the second end of the C-arm.

9. The C-arm x-ray imaging system of claim 8, wherein the mounting structure is configured to constrain translational movement of the photon-counting detector towards the x-ray source along the axial axis, and
wherein the mounting structure includes:
a track coupled to the C-arm; and
a supporting beam coupled to the photon-counting detector, and to the track, and
wherein the track guides translation of the photon-counting detector.

10. The C-arm x-ray imaging system of claim 9, further comprising a wheel coupled to the support beam, the wheel received within the track, and
wherein the wheel rolls along the track to translate the photon-counting detector.

11. The C-arm x-ray imaging system of claim 8, wherein the mounting structure is pivotally coupled to the C-arm at one end, and is coupled to the photon-counting detector at an opposing end.

12. The C-arm x-ray imaging system of claim 1, wherein the energy-integrating x-ray detector is removably coupled to the second end of the C-arm, and
wherein the photon-counting detector is removably coupled to the second end of the C-arm,
wherein when the energy-integrating x-ray detector is coupled to the second end of the C-arm, the photon-counting detector cannot be coupled to the second end of the C-arm, and
wherein when the photon-counting detector is coupled to the second end of the C-arm, the energy-integrating x-ray detector cannot be coupled to the second end of the C-arm.

13. The C-arm x-ray imaging system of claim 12, wherein the energy-integrating x-ray detector and the photon-counting detector are in electrical communication with a processor of the C-arm x-ray imaging system.

14. The C-arm x-ray imaging system of claim 12, wherein when the energy-integrating x-ray detector is coupled to the another end of the C-arm:
the energy-integrating x-ray detector is in electrical communication with a processor of the C-arm x-ray imaging system; and
the photon-counting detector is not in electrical communication with the processor of the C-arm X-ray imaging system, and
wherein when the photon-counting detector is coupled to the another end of the C-arm:
the photon-counting detector is in electrical communication with a processor of the C-arm x-ray imaging system; and
the energy-integrating x-ray detector is not in electrical communication with the processor of the C-arm X-ray imaging system.

15. A method of controlling a C-arm x-ray imaging system including a gantry formed as a C-arm, an x-ray source, and a changeable x-ray detector assembly having an energy-integrating detector and a photon-counting detector, the method comprising:

acquiring first x-ray imaging data, using a processor in communication with the C-arm x-ray imaging system, and only the energy-integrating x-ray detector; and acquiring second x-ray imaging data, using the processor, and only the photon-counting detector.

16. The method of claim 15, wherein the x-ray source assembly defines an axial axis, wherein the axial axis intersects the photon-counting detector and energy-integrating x-ray detector, and further comprising moving the photon-counting detector so that the axial axis no longer intersects the photon-counting detector, prior to acquiring the first x-ray imaging data.

17. The method of claim 16, wherein the energy-integrating x-ray detector has a peripheral edge, and further comprising moving the entire photon-counting detector past the peripheral edge of energy-integrating x-ray detector.

18. The method of claim 16, further comprising moving the photon-counting detector so that the axial axis intersects the photon-counting detector, prior to acquiring second x-ray imaging data.

19. The method of claim 18, further comprising calibrating the photon-counting detector after moving the photon-counting detector, and prior to acquiring the second x-ray imaging data.

20. The method of claim 15, further comprising:
forming a first image using the first x-ray imaging data;
presenting the first image on a display;
forming a second image using the second x-ray imaging data;
presenting the second image on the display.

21. A method of retrofitting a C-arm x-ray imaging system, the method comprising:
providing the C-arm x-ray imaging system having:
a gantry formed as a C-arm;
an x-ray source assembly coupled to one end of the C-arm, the x-ray source assembly defining an axial axis that intersects the x-ray source assembly; and
an x-ray detector assembly coupled to a second end of the C-arm, the x-ray detector having an energy-integrating detector configured to sense x-rays by energy integration over time;
installing a photon-counting detector to the second end of the C-arm; and
moving one of the energy-integrating detector or the photon-counting detector relative to the x-ray source so only one the energy-integrating detector or the photon-counting detector is arranged to receive the x-rays emitted from the x-ray source at a time.

22. The method of claim 21, further comprising installing a mounting system to the second end of the C-arm, the mounting system being coupled to the photon-counting detector and to the second end of the C-arm, and
wherein the photon-counting detector is axially separated from the energy-integrating detector by an axial distance along the axial axis.

23. The method of claim 22, wherein the mounting system includes a track,
wherein a supporting beam is coupled to the photon-counting detector,
wherein the supporting beam is coupled to the track, and
wherein the track guides translation of the photon-counting detector.

24. The method of claim 22, wherein the mounting system is coupled to the photon-counting detector at one end, and
wherein installing the mounting system includes pivotally coupling an opposing end of the mounting system to the second end of the C-arm.

25. The method of claim 21, further comprising calibrating the photon-counting detector after installation of the photon-counting detector.

26. A C-arm x-ray imaging system comprising:
a gantry formed as a C-arm configured to pivot about a pivot axis;
an x-ray source coupled to a first end of the C-arm, the x-ray source configured to emit x-rays along a path extending to define an axial axis; and
both a photon-counting detector and an energy-integrating detector coupled to the second end of the C-arm, wherein the photon-counting detector has a photon-counting sensing surface defined by an array of photon-counting sensing elements that is smaller than an energy-integrating sensing surface defined by an array of energy-integrating sensing elements of the energy-integrating detector.

* * * * *